(12) United States Patent
Binner

(10) Patent No.: US 8,028,500 B2
(45) Date of Patent: Oct. 4, 2011

(54) INTRAVAGINAL DEVICE WITH FLUID TRANSPORT PLATES

(75) Inventor: Curt Binner, Furlong, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 85 days.

(21) Appl. No.: 12/724,739

(22) Filed: Mar. 16, 2010

(65) Prior Publication Data

US 2010/0170069 A1 Jul. 8, 2010

Related U.S. Application Data

(60) Division of application No. 11/478,944, filed on Jun. 30, 2006, now Pat. No. 7,861,494, which is a continuation-in-part of application No. 11/444,792, filed on Jun. 1, 2006, now Pat. No. 7,845,380, which is a continuation-in-part of application No. PCT/US2005/017107, filed on May 13, 2005, which is a continuation-in-part of application No. 10/848,257, filed on May 14, 2004, now abandoned, which is a continuation-in-part of application No. 10/847,951, filed on May 14, 2004.

(60) Provisional application No. 60/572,054, filed on May 14, 2004.

(51) Int. Cl.
*B65B 11/54* (2006.01)

(52) U.S. Cl. ............... 53/438; 53/203; 53/223; 53/409; 53/436

(58) Field of Classification Search .................. 53/396, 53/409, 416, 419, 424, 436, 438, 203, 209, 53/218, 222–224, 226–227, 230–232
See application file for complete search history.

(56) References Cited

U.S. PATENT DOCUMENTS

| | | |
|---|---|---|
| 398,015 A | 2/1889 | Williams |
| 735,729 A | 8/1903 | Dowing |
| 867,176 A | 9/1907 | Warwick |
| 1,731,665 A | 10/1929 | Huebsch |
| 1,926,900 A | 9/1933 | Hasse et. al. |
| 1,941,717 A | 1/1934 | Rabell |
| 2,099,931 A | 11/1937 | Fourness |
| 2,188,923 A | 2/1940 | Robinson |
| 2,265,636 A | 12/1941 | Eaton |
| 2,301,106 A | 11/1942 | Brown |
| 2,306,406 A | 12/1942 | Robinson |
| 2,394,219 A | 2/1946 | Vachon |

(Continued)

FOREIGN PATENT DOCUMENTS

AU 748284 B1 2/2000

(Continued)

*Primary Examiner* — Christopher Harmon

(57) ABSTRACT

An apparatus for producing an absorbent article includes a holding tool, a female tool disposed along a machine axis, and a male tool disposed along the machine axis. The holding tool has an aperture aligned along the machine axis and means for holding a flexible sheet across the aperture. The female tool has at least one folding element extending in a direction radially away from the machine axis, and the male tool has means for holding a fluid storage element and at least one pleating blade extending in a direction radially away from the machine axis. At least two of the holding tool, female tool, and male tool are capable of relative motion along the machine axis. Further the at least one pleating blade and of the male tool and the at least one folding element of the female tool are aligned to permit manipulation of the flexible sheet about the fluid storage element.

7 Claims, 20 Drawing Sheets

U.S. PATENT DOCUMENTS

| | | | |
|---|---|---|---|
| 2,412,861 A | 12/1946 | George et al. | |
| 2,425,004 A | 8/1947 | Rabell | |
| 2,464,310 A | 3/1949 | Harwoord | |
| 2,624,993 A | 1/1953 | Robertson | |
| 2,830,417 A | 4/1958 | Ullman et al. | |
| 3,007,377 A | 11/1961 | Muller | |
| 3,055,369 A | 9/1962 | Graham, Jr. | |
| 3,135,262 A | 6/1964 | Kobler et al. | |
| 3,340,874 A | 9/1967 | Burgeni | |
| 3,422,496 A | 1/1969 | Wolff | |
| 3,431,909 A | 3/1969 | Krusko | |
| 3,610,243 A | 10/1971 | Jones, Sr. | |
| 3,618,605 A | 11/1971 | Glassman | |
| 3,710,793 A | 1/1973 | Glassman | |
| 3,731,687 A | 5/1973 | Glassman | |
| 3,732,866 A | 5/1973 | Accavallo | |
| 3,811,445 A | 5/1974 | Dostal | |
| 3,845,766 A | 11/1974 | Zoller | |
| 3,851,440 A | 12/1974 | Horsky | |
| 3,929,135 A | 12/1975 | Thompson | |
| RE28,674 E | 1/1976 | Guyette | |
| 3,983,875 A | 10/1976 | Truman | |
| 3,986,511 A | 10/1976 | Olofsson et al. | |
| 4,211,225 A | 7/1980 | Sibalis | |
| 4,212,301 A | 7/1980 | Johnson | |
| 4,335,720 A | 6/1982 | Glassman | |
| 4,341,214 A | 7/1982 | Fries et al. | |
| 4,342,314 A | 8/1982 | Radel et al. | |
| 4,351,339 A | 9/1982 | Sneider et al. | |
| 4,359,357 A | 11/1982 | Fries et al. | |
| 4,372,312 A | 2/1983 | Fendler et al. | |
| 4,381,326 A | 4/1983 | Kelly | |
| 4,508,256 A | 4/1985 | Radel et al. | |
| 4,510,735 A | 4/1985 | Cillario | |
| 4,525,983 A | 7/1985 | Libow | |
| 4,543,098 A | 9/1985 | Wolfe et al. | |
| 4,661,101 A | 4/1987 | Sustmann | |
| 4,675,217 A | 6/1987 | Forsman | |
| 4,685,178 A | 8/1987 | Nakanishi | |
| 4,710,186 A | 12/1987 | DeRossett et al. | |
| 4,816,100 A | 3/1989 | Friese | |
| 5,004,467 A | 4/1991 | Hinzmann et al. | |
| 5,165,152 A | 11/1992 | Kramer et al. | |
| 5,273,596 A | 12/1993 | Newkirk | |
| 5,295,984 A | 3/1994 | Contente et al. | |
| 5,387,209 A | 2/1995 | Yamamoto et al. | |
| 5,403,300 A | 4/1995 | Howarth | |
| 5,500,270 A | 3/1996 | Langdon et al. | |
| 5,545,155 A | 8/1996 | Hseih et al. | |
| 5,567,376 A | 10/1996 | Turi et al. | |
| 5,688,260 A | 11/1997 | Blanton et al. | |
| 5,759,569 A | 6/1998 | Hird et al. | |
| 5,782,063 A | 7/1998 | Boriani et al. | |
| 5,802,806 A | 9/1998 | Scaliti | |
| 5,817,077 A | 10/1998 | Foley et al. | |
| 5,911,712 A | 6/1999 | Leutwyler et al. | |
| 5,928,184 A | 7/1999 | Etheredge et al. | |
| 5,972,505 A | 10/1999 | Phillips et al. | |
| 6,177,606 B1 | 1/2001 | Etheredge et al. | |
| 6,177,608 B1 | 1/2001 | Weinstrauch | |
| 6,183,436 B1 | 2/2001 | Korteweg et al. | |
| 6,191,341 B1 | 2/2001 | Shippert | |
| 6,206,867 B1 | 3/2001 | Osborn et al. | |
| 6,310,269 B1 | 10/2001 | Friese et al. | |
| 6,358,235 B1 | 3/2002 | Osborn et al. | |
| 6,433,246 B1 | 8/2002 | Nguyen et al. | |
| 6,436,328 B1 | 8/2002 | DiPalma | |
| 6,465,713 B1 | 10/2002 | Gell et al. | |
| 6,479,728 B1 | 11/2002 | DiPalma | |
| 6,554,814 B1 | 4/2003 | Agyapont et al. | |
| 6,558,362 B1 | 5/2003 | Chaffringeon | |
| 6,570,055 B2 | 5/2003 | Yang et al. | |
| 6,595,974 B1 | 7/2003 | Pauley et al. | |
| 6,635,800 B2 | 10/2003 | Jackson et al. | |
| 6,719,743 B1 | 4/2004 | Wada | |
| 6,840,927 B2 | 1/2005 | Hasse et al. | |
| 6,860,874 B2 | 3/2005 | Gubernick et al. | |
| 6,889,409 B2 * | 5/2005 | Friese et al. | 28/118 |
| 7,059,026 B2 * | 6/2006 | Friese et al. | 28/118 |
| 7,101,358 B2 | 9/2006 | Domeier et al. | |
| 7,112,192 B2 | 9/2006 | Hasse et al. | |
| 7,160,279 B2 | 1/2007 | Pauley et al. | |
| 7,179,952 B2 | 2/2007 | Vukos et al. | |
| 7,335,194 B2 | 2/2008 | Wada | |
| 7,618,403 B2 | 11/2009 | Carasso et al. | |
| 2002/0012373 A1 | 1/2002 | Yokozeki et al. | |
| 2002/0026177 A1 | 2/2002 | Lochte et al. | |
| 2002/0133135 A1 | 9/2002 | Gell et al. | |
| 2002/0138035 A1 | 9/2002 | Hull, Jr. | |
| 2002/0157222 A1 * | 10/2002 | Friese et al. | 28/118 |
| 2003/0093049 A1 | 5/2003 | Johnson et al. | |
| 2003/0097106 A1 | 5/2003 | Hasse et al. | |
| 2003/0097108 A1 | 5/2003 | Hasse et al. | |
| 2003/0105444 A1 | 6/2003 | Lochte et al. | |
| 2003/0135180 A1 | 7/2003 | Nguyen et al. | |
| 2003/0149416 A1 | 8/2003 | Cole et al. | |
| 2003/0208179 A1 * | 11/2003 | Fuchs et al. | 604/385.17 |
| 2003/0208180 A1 * | 11/2003 | Fuchs et al. | 604/385.17 |
| 2003/0229328 A1 | 12/2003 | Costa | |
| 2004/0127879 A1 | 7/2004 | Pauley et al. | |
| 2004/0147896 A1 | 7/2004 | Mizutani et al. | |
| 2005/0256482 A1 | 11/2005 | Minoguchi et al. | |
| 2005/0256484 A1 | 11/2005 | Chase et al. | |
| 2005/0256485 A1 | 11/2005 | Carasso et al. | |
| 2005/0256486 A1 | 11/2005 | Carasso et al. | |
| 2005/0256511 A1 | 11/2005 | Chase et al. | |
| 2005/0277904 A1 | 12/2005 | Chase et al. | |
| 2005/0283128 A1 | 12/2005 | Chase et al. | |
| 2006/0004338 A1 | 1/2006 | Torkildsen et al. | |
| 2006/0217677 A1 | 9/2006 | Chase et al. | |
| 2006/0235361 A1 | 10/2006 | Agyapong et al. | |
| 2007/0010388 A1 | 1/2007 | Binner | |
| 2007/0049893 A1 | 3/2007 | Binner et al. | |
| 2007/0282289 A1 | 12/2007 | Carasso et al. | |
| 2008/0255495 A1 | 10/2008 | Chase et al. | |
| 2009/0171310 A1 | 7/2009 | Carasso et al. | |
| 2009/0177173 A1 | 7/2009 | Chase et al. | |
| 2009/0260205 A1 | 10/2009 | Binner | |
| 2010/0069866 A1 | 3/2010 | Binner et al. | |
| 2010/0168645 A1 | 7/2010 | Binner et al. | |
| 2010/0170069 A1 | 7/2010 | Binner | |
| 2010/0192339 A1 | 8/2010 | Binner et al. | |

FOREIGN PATENT DOCUMENTS

| | | |
|---|---|---|
| CA | 2293599 A1 | 6/2001 |
| EP | 1 108 408 | 6/2001 |
| GB | 2292526 A | 2/1996 |
| JP | 48020395 A | 3/1973 |
| JP | 52020799 U | 2/1977 |
| JP | 53163894 U | 12/1978 |
| JP | 56090225 U | 7/1981 |
| JP | 60171044 A | 9/1985 |
| JP | 62155835 U | 10/1987 |
| JP | 3198850 A | 8/1991 |
| JP | 04120734 U | 10/1992 |
| JP | 59528 U | 2/1993 |
| JP | 9510374 T | 10/1997 |
| JP | 2002508216 T | 3/2002 |
| JP | 2004508892 T | 3/2004 |
| WO | WO 83/03537 A | 10/1983 |
| WO | WO 95/24877 A | 9/1995 |
| WO | WO 96/00552 A1 | 1/1996 |
| WO | WO 97/09017 A | 3/1997 |
| WO | WO 99/00063 A1 | 1/1999 |
| WO | WO 99/30659 A | 6/1999 |
| WO | WO 00/61052 A | 10/2000 |
| WO | WO 01/01906 A1 | 1/2001 |
| WO | WO 99/00096 A1 | 1/2001 |
| WO | WO 02/24133 A | 3/2002 |
| WO | WO 02/058609 A | 8/2002 |
| WO | WO 02/076357 A | 10/2002 |
| WO | WO 2005/112856 A | 12/2005 |

* cited by examiner

INTRAVAGINAL DEVICE WITH FLUID TRANSPORT PLATES

CROSS-REFERENCE TO RELATED APPLICATIONS

This application is a divisional of U.S. application Ser. No. 11/478,944, filed on Jun. 30, 2006 now U.S. Pat. No. 7,861,494, which is a continuation-in-part of U.S. application Ser. No. 11/444,792, filed on Jun. 1, 2006 now U.S. Pat. No. 7,845,380, and a continuation-in-part of international application PCT/US2005/017107 filed May 13, 2005, which claims the benefit of 60/572,054 filed on May 14, 2004, and a continuation-in-part of U.S. application Ser. No. 10/848,257 filed on May 14, 2004 now abandoned, and a continuation-in-part of U.S. application Ser. No. 10/847,951 filed on May 14, 2004, the content of each of which is incorporated herein.

This invention is related to the following applications: U.S. application Ser. No. 10/847,952, filed on May 14, 2004 (US publication 2005-0256511-A1), U.S. application Ser. No. 10/848,347, filed on May 14, 2004 (US publication 2005-0256485-A1), and U.S. application Ser. No. 10/848,208, filed on May 14, 2004 (US publication 2005-0256484-A1), the content of each of which is incorporated herein.

FIELD OF THE INVENTION

The present invention relates to devices for capturing and storing body fluid intravaginally. More particularly, the present invention relates to a method of capturing body fluid intravaginally via a fluid transport element and transporting the body fluid to a fluid storage element where the fluid is stored. Additionally, this application relates to methods of making such devices

BACKGROUND OF THE INVENTION

Devices for capturing and storing bodily fluid intravaginally are commercially available and known in the literature. Intravaginal tampons are the most common example of such devices. Commercially available tampons are generally compressed cylindrical masses of absorbent fibers that may be over-wrapped with an absorbent or nonabsorbent cover layer.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

A drawback often encountered with commercially available tampons is the tendency toward premature failure, which may be defined as bodily fluid leakage from the vagina while the tampon is in place, and before the tampon is completely saturated with the bodily fluid. The patent art typically describes a problem believed to occur that an unexpanded, compressed tampon is unable to immediately absorb fluid. Therefore, it presumes that premature leakage may occur when bodily fluid contacts a portion of the compressed tampon, and the fluid is not readily absorbed. The bodily fluid may bypass the tampon.

To overcome this problem of premature leakage, extra elements have been incorporated into a basic tampon to try to direct and control the flow of fluid toward the absorbent core.

For example, U.S. Pat. No. 4,212,301 (Johnson) discloses a unitary constructed digital tampon having a lower portion compressed preferably in the radial direction to form a rigid, rod-like element, which provides a central rigidified elongated core and an upper portion left substantially uncompressed. After insertion, the uncompressed portion may be manipulated to contact the vaginal wall to provide an immediate seal against side leakage. The uncompressed portion allows for high absorbent capacity immediately upon insertion. While this tampon may allow for a certain amount of protection from bypass leakage, the uncompressed portion may become saturated before the compressed portion has a chance to expand and become absorbent.

U.S. Pat. No. 6,358,235 (Osborn et al.) discloses a "hollow" bag-like tampon that may have an interior projection made from highly compressed absorbent material. The interior projection is preferably attached to the inside surface of the head of the tampon. The hollow tampon portion may include at least one pleat in the absorbent outer surface and is soft and conformable. The tampon is not pre-compressed to the point where the fibers temporarily "set" and re-expand upon the absorption of fluid. The absorbent portions of the tampon can saturate locally, which leads to bypass leakage.

U.S. Pat. No. 6,177,608 (Weinstrauch) discloses a tampon having nonwoven barrier strips that are outwardly spreadable from the tampon surface to reliably close the free spaces believed to exist within a vaginal cavity. The nonwoven barrier strips extend about the tampon in a circumferential direction at the surface or in a helical configuration about the tampon and purportedly conduct menstrual fluid toward the tampon surface. The nonwoven barrier strips are attached to the cover by means of gluing, heat bonding, needle punching, embossing or the like and form pleats. The nonwoven barrier strips are attached to the tampon blank and the blank is embossed, forming grooves extending in a longitudinal direction. While this tampon purports to direct fluid to the core, it attempts to achieve this by forming pockets of absorbent nonwoven fabric. In order to function, it appears that these pockets would have to be opened during use to allow fluid to enter. However, based upon current understandings of vaginal pressures, it is not understood how the described structure could form such an opened volume.

U.S. Pat. No. 6,206,867 (Osborn) suggests that a desirable tampon has at least a portion of which is dry expanding to cover a significant portion of the vaginal interior immediately upon deployment. To address this desire, it discloses a tampon having a compressed central absorbent core having at least one flexible panel attached along a portion of the side surface of the core. The flexible panel appears to provide the "dry-expanding" function, and it extends outwardly from the core away from the point of attachment. The flexible panel contacts the inner surfaces of the vagina when the tampon is in place and purportedly directs fluid toward the absorbent core. The flexible panel is typically attached to the pledget prior to compression of the pledget to form the absorbent core and remains in an uncompressed state.

U.S. Pat. No. 5,817,077 (Foley et al.) discloses a method of preserving natural moisture of vaginal epithelial tissue while a using a tampon where the tampon has an initial capillary suction pressure at the outer surface of less than about 40 mm Hg. This allows the tampon to absorb vaginal secretions without substantially drying the vaginal epithelial tissue. The multiple cover layers can be used to increase the thickness of the cover material. While this represents a significant advancement in the art, this invention does not address bypass leakage.

Additionally, U.S. Pat. No. 5,545,155 (Hseih et al.) discloses an external absorbent article that has a set of plates separated by spacer elements. The plates may be treated to affect wettability so that fluid will flow easily across the surface. Extending through the upper plate is a plurality of openings, which allow fluid to flow with little restriction into the space between the upper and lower plates. When the fluid flows downward in the z-direction from the upper plate to the lower plate, it will then flow laterally in the x- and y-directions. Therefore, this external absorbent article can contain fluid gushes, but it does not appear to address the problems relating in particular to intravaginal devices, such as a tampon.

While the prior art is replete with examples of sanitary protection articles that capture bodily fluids both externally and intravaginally, these examples do not overcome the problem of premature failure often identified as by-pass leakage that commonly occurs while using internal sanitary protection devices. Many solutions to this problem have involved increasing the rate of expansion of a highly compressed absorbent article.

SUMMARY OF THE INVENTION

Surprisingly, we have found a novel way to address the problem of premature failure. This invention is not dependent on the expansion of the compressed absorbent but rather incorporating an element, which is adaptable to the vagina. In our invention, we increase the contact area of the absorbent device and thereby reduce by-pass leakage.

In one aspect of the invention, the intravaginal device has a fluid storage element; a fluid transport element having a first plate having an outwardly oriented surface and an inwardly oriented surface; a second plate that has a first surface disposed in facing relationship with the inwardly oriented surface of the first plate and an opposite surface, and that is capable of separating from the first plate sufficiently to provide inter-plate capillary action. The fluid transport element is in fluid communication with the fluid storage element and substantially encases the fluid storage element, wherein at least a portion of the outwardly oriented surface of the first plate is capable of contacting a user's vaginal epithelium.

In another aspect of the invention, the intravaginal device has a fluid storage element having an insertion end and a withdrawal end and a fluid transport element having a first plate having an outwardly oriented surface and an inwardly oriented surface; a second plate that has a first surface disposed in facing relationship with the inwardly oriented surface of the first plate, and an opposite surface, and that is capable of separating from the first plate sufficiently to provide inter-plate capillary action. The fluid transport element is in fluid communication with the fluid storage element and substantially encases the fluid storage element. A withdrawal string is attached to the fluid storage element such that the fluid transport element is bonded to the withdrawal string at the withdrawal end of the fluid storage element, wherein at least a portion of the outwardly oriented surface of the first plate is capable of contacting a user's vaginal epithelium.

In still another aspect of the invention, the intravaginal device has a fluid storage element having an insertion end and withdrawal end; a fluid transport element having a first plate having an outwardly oriented surface and an inwardly oriented surface; a second plate that has a first surface disposed in facing relationship with the inwardly oriented surface of the first plate and an opposite surface, and that is capable of separating from the first plate sufficiently to provide inter-plate capillary action. The fluid transport element is in fluid communication with the fluid storage element and substantially encases the fluid storage element, wherein the fluid storage element is attached to the withdrawal end of the fluid storage element.

In yet another aspect of the invention, the intravaginal device has a fluid storage element having an insertion end, a withdrawal end, and longitudinal sides therebetween; a fluid transport element having a first plate having an outwardly oriented surface and an inwardly oriented surface; a second plate that has a first surface disposed in facing relationship with the inwardly oriented surface of the first plate and an opposite surface, and that is capable of separating from the first plate sufficiently to provide inter-plate capillary action. The fluid transport element is in fluid communication with the fluid storage element and substantially encases the fluid storage element, and wherein the fluid transport element is attached to the fluid storage element on at least one longitudinal side.

In still yet another aspect of the invention, the intravaginal device has a fluid storage element having an insertion end, a withdrawal end, and at least one longitudinal side therebetween; a fluid transport element having a first plate having an outwardly oriented surface and an inwardly oriented surface; a second plate that has a first surface disposed in facing relationship with the inwardly oriented surface of the first plate, and an opposite surface, and that is capable of separating from the first plate sufficiently to provide inter-plate capillary action. The fluid transport element in fluid communication with the fluid storage element wherein the fluid transport element is attached to the fluid storage element on at least one longitudinal side.

In still yet another aspect of the invention, the intravaginal device has a fluid storage element having an insertion end, a withdrawal end, and at least one longitudinal side therebetween; a fluid transport element having a first plate having an outwardly oriented surface and an inwardly oriented surface; a second plate that has a first surface disposed in facing relationship with the inwardly oriented surface of the first plate, and an opposite surface, and that is capable of separating from the first plate sufficiently to provide inter-plate capillary action. The fluid transport element is in fluid communication with the fluid storage element wherein the at least one longitudinal side has at least one outward surface and one inward surface and the fluid transport element is attached to the outward surface of the fluid storage element.

In still yet another aspect of the invention, the intravaginal device has a fluid transport element having a first plate having an outwardly oriented surface and an inwardly oriented surface; a second plate that has a first surface disposed in facing relationship with the inwardly oriented surface of the first plate, and an opposite surface, and that is capable of separating from the first plate sufficiently to provide inter-plate capillary action; and a fluid storage element in fluid communication with the fluid transport element, the fluid storage element has an insertion end and a withdrawal end and the fluid transport element is attached to the fluid storage element at the insertion end.

The fluid transport element may be thermobondable, attached longitudinally, and include multiple plates.

Other aspects and features of the present invention will become apparent to those ordinarily skilled in the art upon review of the following description of specific embodiments of the invention in conjunction with the accompanying drawings.

BRIEF DESCRIPTION OF THE DRAWING

FIG. 2a shows a perspective view of a tampon having a plurality of fluid transport elements extending therefrom that are formed from a folded sheet material.

FIG. 2b shows a side elevation of the tampon with a plurality of fluid transport elements wrapped around the fluid storage element.

FIG. 2c shows a transverse cross-section along line 2c-2c in FIG. 2b.

FIG. 2d shows a side elevation of the tampon of FIG. 2a.

FIG. 2e shows a top elevation of the tampon of FIG. 2a.

DETAILED DESCRIPTION OF THE PREFERRED EMBODIMENTS

Figure 1A:
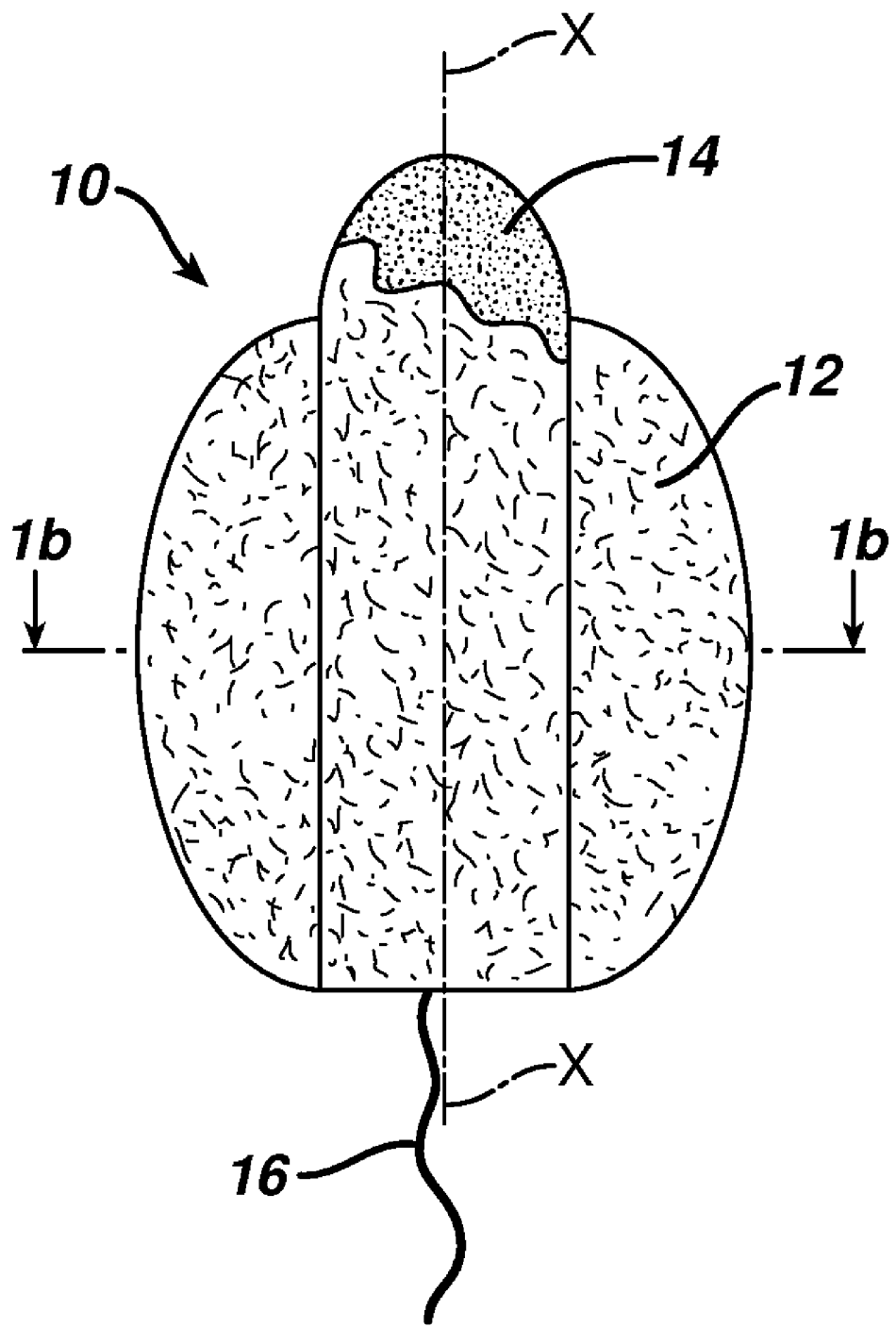
FIG. 1a shows a side elevation of an intravaginal device having a fluid transport element in fluid communication with a fluid storage element.

As used herein in the Specification and the Claims, the term "bodily fluid" and variants thereof mean bodily exudates, especially liquids that are produced by, secreted by, emanate from, and/or discharged from a human body.

As used herein in the Specification and the Claims, the term "fluids" and variants thereof relate to liquids, and especially bodily fluids.

As used herein in the Specification and the Claims, the term "sheet" and variants thereof relates to a portion of something that is thin in comparison to its length and breadth.

As used herein in the Specification and the Claims, the term "parallel plate" and variants thereof relates to a system of at least two relatively parallel sheets that are capable of moving fluids through inter-plate capillary action. The individual "plates" in the system may be flexible and/or resilient in order to move within their environment. However, they may be maintained in a substantially facing relationship with relatively constant separation at least in a localized portion of their structure (as compared with their relative length and width). Thus, two sheets could be fluted, but if the flutes were "nested", the sheets would generally remain generally parallel in any given localized portion.

As used herein in the Specification and the Claims, the term "inter-plate capillary action" and variants thereof mean the movement of fluid due to a pressure difference across a liquid-air meniscus created within a gap between two substantially parallel plates. The two plates need not be held apart a specific distance, although they should be separable to allow fluid to move between them by inter-plate capillary action. A general equation providing the rise of a fluid between parallel plates is reported as:

$$h = \frac{2\sigma * \cos\theta}{\rho * g * d}$$

in which:
h is rise of fluid between plates
σ is the surface tension of fluid in contact w/plate
θ is contact angle
ρ is density
d is distance between plates, and
g is the gravitational constant Therefore, as long as the contact angle, θ, is less than 90°, there will be some capillary attraction.

As used herein in the Specification and the Claims, the term "porous medium" and variants thereof relates to a connected 3-dimensional solid matrix with a highly ramified network of pores and pore throats in which fluids may flow.

As used herein in the Specification and the Claims, the term "separable plates" and variants thereof mean any condition of separation of the first plate and the second plate, which allows fluid to move between the plates. This includes situations in which facing surfaces of adjacent first and second plates are touching one another in portions of or across substantially all of their facing surfaces. This also includes situations in which the facing surfaces of the adjacent first and second plates are separably joined together such that upon contact with fluid, the surfaces separate enough to provide for fluid to move between them. This further includes situations in which facing surfaces of adjacent first and second plates are joined together, as long as fluid may still move freely between the surfaces.

As used herein in the Specification and the Claims, the term "in fluid communication" and variants thereof relate to elements that are arranged and configured to allow fluid to move therebetween.

As used herein in the Specification and the Claims, the term "coupled" and variants thereof relate to the relationship between two portions of an integral structure that are either portions of the same material (e.g., two portions of a folded sheet) or are materials that are joined together (e.g., two separate sheets that are bonded together).

As used herein in the Specification and the Claims, the term "fluid pervious" and variants thereof relate to a material that permits fluid or moisture to pass through without additional processing, such as aperturing. Therefore, for example, an untreated woven or nonwoven material is fluid pervious and a continuous, plastic film or metal foil is not. A nonwoven permits fluid flow via the interstices between fibers, such that fluid can flow through, either by capillary action and/or via a pressure differential from one side of the nonwoven to the other such as the pressure experienced by a tampon in use.

Figure 1B:
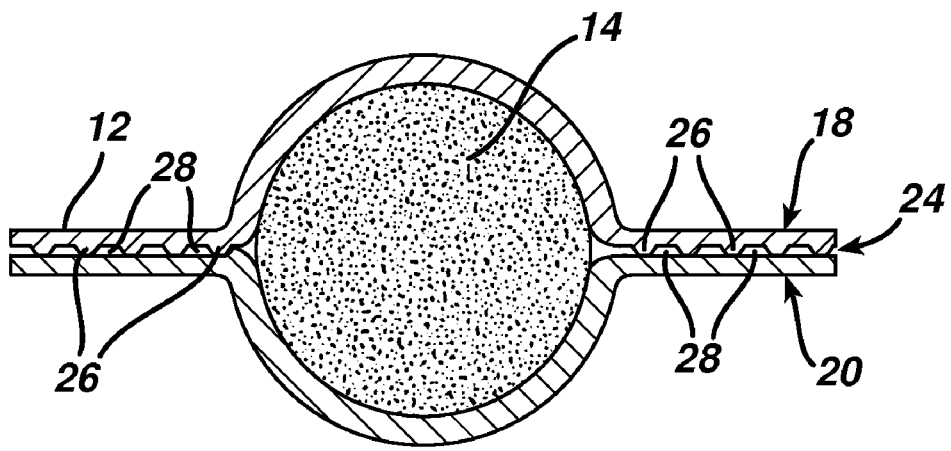
FIG. 1b shows a cross-sectional view of the device in FIG. 1a taken along line b-b.
Figure 1C:
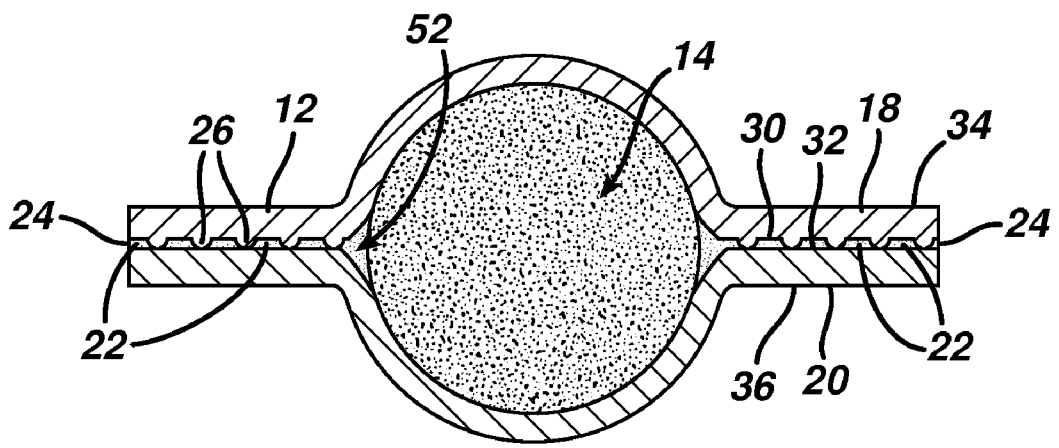
FIG. 1c shows the transverse cross-section shown in 1b, after the introduction of a fluid between the plates of the fluid acquisition element.

Referring to FIGS. 1a-1c, this invention provides an intravaginal device 10 having at least one fluid transport element 12 in fluid communication with a fluid storage element 14 (FIGS. 1a-1c show two fluid transport elements 12 located on opposite sides of the fluid storage element 14). The device may also include a withdrawal mechanism, such as a string 16.

The fluid storage element can be any convenient shape including cylindrical, cup like, hourglass, spherical, etc. It can be an absorbent or a fluid collection device. It can be in separate sections with the fluid transport element(s) bridging or connecting the sections.

The storage element can be made of any material known in the art such as cotton, rayon, polyester, superabsorbent materials, and the like. The fluid storage element can be made of any composition known in the art, such as compressed fibrous webs, rolled goods, foam, and the like. The material may be formed as a unitary mass or a plurality of discrete particles or agglomerations. The material may be compressed to maintain a relatively stable form, or it may be left relatively uncompressed. For example, the absorbent material may include a central portion of absorbent wood pulp material. The pulp may be covered by a thin absorbent woven or nonwoven fabric and may be coterminous with the fluff pad or completely envelop it on all sides. Absorbent materials which are uncompressed or of low density have a much higher holding capacity for fluids than high density materials. A consideration for using uncompressed materials is the bulk or volume that may be required in order to achieve sufficient absorbency.

In one preferred embodiment, the fluid storage element 14 is an absorbent tampon. Absorbent tampons are usually substantially cylindrical masses of compressed absorbent material having a central axis and a radius that defines the outer circumferential surface of the tampon. Such tampons are disclosed in e.g., Haas, U.S. Pat. No. 1,926,900; Dostal, U.S. Pat. No. 3,811,445; Wolff, U.S. Pat. No. 3,422,496; Friese et al., U.S. Pat. No. 6,310,296; Leutwyler et al., U.S. Pat. No. 5,911,712, Truman, U.S. Pat. No. 3,983,875; Agyapong et al., U.S. Pat. No. 6,554,814. Tampons also usually include a fluid-permeable cover (which may include or be replaced by another surface treatment) and a withdrawal string or other removal mechanism.

Absorbent materials useful in the formation of the absorbent body include fiber, foam, superabsorbent, hydrogels, and the like. Preferred absorbent material for the present invention includes foam and fiber. Absorbent foams may include hydrophilic foams, foams that are readily wetted by aqueous fluids as well as foams in which the cell walls that form the foam themselves absorb fluid.

Fibers may be selected from cellulosic fiber, including natural fibers (such as cotton, wood pulp, jute, and the like) and synthetic fibers (such as regenerated cellulose, cellulose nitrate, cellulose acetate, rayon, polyester, polyvinyl alcohol, polyolefin, polyamine, polyamide, polyacrylonitrile, and the like).

The fluid storage element may also be in the form of a collection cup. Examples of such devices are disclosed in Zoller, U.S. Pat. No. 3,845,766 and Contente et al., U.S. Pat. No. 5,295,984. Collection devices are designed to assume a normally open, concave configuration, with an open side facing a user's cervix. The collection devices may be folded, or otherwise manipulated, to facilitate insertion into the vaginal canal The fluid transport element has at least a first plate 18 and a second plate 20. The first and second plates combine to provide a set of parallel plates, and the fluid transport elements 12 are shown as extending radially away from the fluid storage element 14. Additional plates may also be incorporated into each fluid transport element 12.

The plates are configured and arranged to allow the introduction of bodily fluid 22 to separate a plate from adjacent plate(s) (FIG. 1c). At least one opening 24 allows the introduction of bodily fluids 22. Optionally, one or more spacer elements 26 can be inserted to establish and to maintain space between adjacent plates.

FIG. 1b shows a pair of parallel plates prior to the introduction of a fluid. In this view, the facing surfaces of the adjacent plates 18, 20 are in contact. On the other hand, FIG. 1c shows the set of parallel plates separated by a bodily fluid 22, providing an inter-plate capillary gap 28 between the inwardly oriented surface 30 of the first plate 18 and the first surface 32 of the second plate 20. This inter-plate capillary gap 28 is sufficient to provide inter-plate capillary action to allow the fluid transport element 12 to acquire, to spread, and to move bodily fluids 22 from the vagina to the fluid storage element 14. The first plate 18 also has an outwardly oriented surface 34, and the second plate 20 also has an opposite surface 36.

The plates 18, 20 can be made of almost any hydrophobic or hydrophilic material, preferably sheet-like. The thickness of each plate is not critical. However, it can preferably be selected from the range of from about 0.005 to about 0.050 inch. The materials of construction and the thickness of the plates should be designed so that they are sufficiently stiff and/or resistant to wet collapse when exposed to fluid. Preferably, the sheet-like material is a relatively smooth nonwoven material. If the fluid storage element has properties appropriate for the fluid transport element, the two elements may be formed of the same material.

In particular, materials useful for forming the fluid transport element may have properties such as thermobondability to provide means to incorporate it into the intravaginal device. A representative, non-limiting list of useful materials includes polyolefins, such as polypropylene and polyethylene; polyolefin copolymers, such as ethylenevinyl acetate ("EVA"), ethylene-propylene, ethyleneacrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. The fluid transport element may also be micro-embossed or apertured.

The fluid transport element 12 may also be constructed from a tissue or layers of tissue. One suitable tissue is an airlaid tissue available from Fort Howard Tissue Company of Green Bay, Wis., and having a basis weight of about 35 lbs./3000 ft$^2$. Another suitable airlaid tissue is available from Merfin Hygenic Products, Ltd., of Delta, British Columbia, Canada, having a basis weight of about 61 lbs./3000 ft$^2$ and having the designation grade number 176.

As previously stated, the fluid transport element may be made from a fibrous nonwoven material. In one embodiment, the nonwoven material can be made from natural fibers, synthetic fibers, or a blend of synthetic and natural fibers that permit fluid to pass through to a fluid storage element. The nonwoven material can be hydrophilic or hydrophobic. The cover material can be used as is or can be apertured by methods known in the art to be an apertured, fluid pervious material. Apertures permit relatively viscous fluid, or fluid having some solids content, such as menses, to pass relatively unimpeded through the fluid pervious material such that it can be readily absorbed by the fluid storage element. The apertures permit the fluid, such as menses, to penetrate deeper into the article to improve the masking property of the article. Therefore, the fluid pervious, preferably nonwoven, fluid transport element of the present invention permits fluid transport to and absorption into the fluid storage element.

In one embodiment, the fluid transport element is hydrophobic, or rendered hydrophobic, such that absorbed fluid is attracted to, or remains in, the fluid storage element, not in the fluid transport element. Because of the relatively poor wicking propensity of the hydrophobic fluid transport element, the fluid transport element remains relatively free of menses, giving a cleaner visual appearance to the post-use intravaginal device. In one embodiment, apertures provide for improved fluid flow into the core, and better visual appearance post use. By providing apertures in the fluid transport element, fluid absorption of relatively viscous fluid can be enhanced due to the lack of any obstruction to fluid absorption via the apertures. The cover remains relatively free of menses, and appears less soiled and closer to it original appearance. This provides the appearance of overall cleanliness.

It may be helpful to keep the exposed surface of the fluid transport element as smooth as possible. It may also be helpful to provide it with a low coefficient of friction. These characteristics may provide at least two benefits: (1) the force required to insert the intravaginal device is reduced, and (2) it reduces the damage otherwise caused by scraping of soft, tender vaginal tissue during insertion, wearing and removal.

Plates 18 and 20 may be made from the same material or alternately, plate 18 may be made from a different material than plate 20.

The parallel plates can have any physical structure to provide a resistance to fluid flow vector in the direction parallel to the inwardly oriented surface 30 of the first plate 18 and the first surface 32 of the second plate 20 that is less than the resistance to fluid flow vector in the direction perpendicular to the plates. Preferably, the plates are made from any smooth material with a non-fibrous surface and are able to transport fluid between the two layers.

The fluid transport element 12 should be strong enough to prevent rupturing during handling, insertion, and removal and to withstand vaginal pressures during use.

It is preferable that the surfaces of the fluid transport element 12 are sufficiently wettable by the bodily fluids that the intravaginal device 10 is intended to collect (this results largely from a correlation of the surface energy of the plate surface and the bodily fluid(s)). Thus, the bodily fluid will easily wet the plate, and capillarity between the plates will draw these bodily fluids from a source to a fluid storage element that is in fluid communication with the fluid transport element.

Surface treatments can be used to modify the surface energy of the plates 18, 20. In a preferred embodiment a surfactant is applied to increase the wettability of the outer or inner surfaces of the parallel plates. This will increase the rate at which the bodily fluids are drawn into and spread between a pair of plates. The surfactant can be applied uniformly to either the inner or outer surfaces or it could be applied with varying coating weights in different regions.

A useful measure to determine the wettability of a plate surface is its contact angle with 1.0% saline. Preferably, the contact angle with 1.0% saline is less than about 90 degrees.

In order to accomplish this, the materials of plates can be chosen from those materials that are known in the art to have low energy surfaces. It is also possible and useful to coat materials that have high-energy surfaces with a surface additive, such as a non-ionic surfactant (e.g., ethoxylates), a diol, or mixtures thereof, in order to increase their wettability by bodily fluids. Such additives are well known in the art, and examples include those described in Yang et al., US App. No. 2002-0123731-A1, and U.S. Pat. No. 6,570,055. Other means of increasing wettability can also be used, such as by corona discharge treatment of, for example, polyethylene or polypropylene, or by caustic etching of, for example, polyester.

The parallel plates forming the fluid transport element can be of any flexibility as long as the material is able to transport fluid to the fluid storage element while the device is in use. It is also preferable that the fluid transport element be sufficiently flexible to provide the user with comfort while inserting, wearing, and removing the device.

The surfaces of the first and second plates facing each other can have a variety of surface textures, ranging from smooth to highly textured. The texturing element may be included as a spacer 26.

The value of spacers 26 or texture may be based on the material's ability to withstand wet collapse when simultaneously subjected to compressive forces and fluid.

The spacer elements 26 can be separate elements applied to one or more of the plates, or they can be integral portions of a plate that extend away from one of the plate's major surfaces. A representative list of such separate spacer elements includes, without limitation, foamed materials such as polystyrene foam; particles such as beads and crystals; discontinuous material such as netting, thread, wax, adhesive, any discrete element that causes a separation between the plates and the like.

Integral spacer elements can be thickened portions of the plate material or deformations of the plate material. A representative list of such an integral spacer element includes, without limitation, nubbles, embossments, corrugations, deformations, and the like. Included in this definition are surface treatments that permanently bond a secondary material to a surface of a first. The spacer elements also increase the texture of the plates. While not wishing to be held to this theory, it is believed that the texturing reduces the viscosity of the fluid being transported. The texture can also be in a gradient. For example, in one embodiment, the texture of the plates has a gradient from smooth near the edge of the plates where the fluid enters the fluid transport element to more textured where the fluid is absorbed.

In order to maintain stability against sliding of the plates with respect to each other and changing of the space between them, it is acceptable, and may be preferable, to secure some local areas of contact between the spacer elements 26 and the adjacent plate or even between spacer elements 26 of two adjacent plates. The plates may be secured through means known to those of ordinary skill in the art. A representative list of such securing means includes, without limitation, thermobonding, adhering, crimping, embossing, ultrasonic bonding or welding, and the like. The adhesive may be applied between the spacer elements and the first and second plates. Preferably, the adhesive is wettable.

Figure 2A:
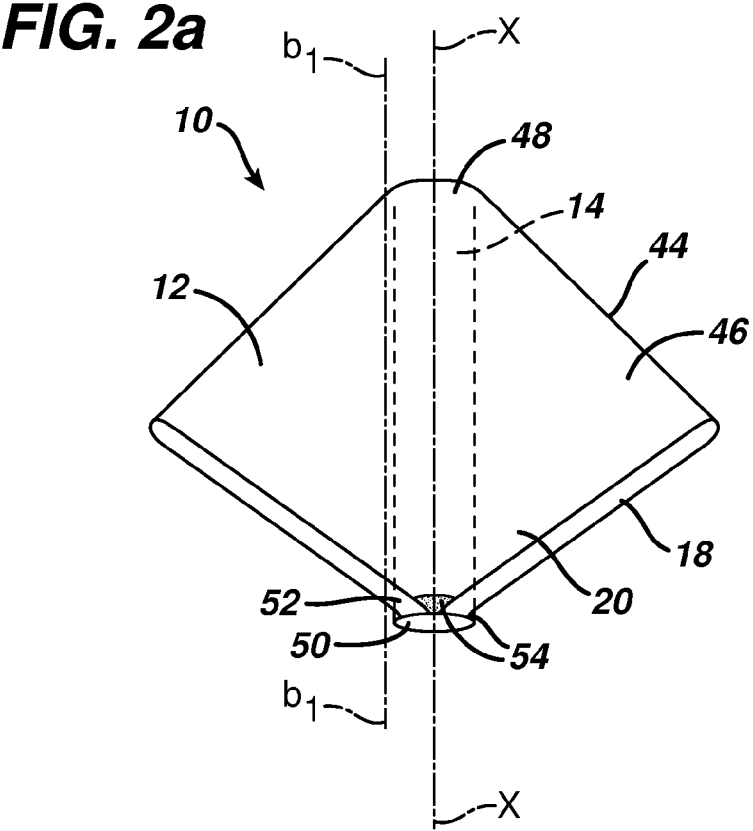
FIGS. 2a-e show various aspects and orientations of an intravaginal device of the present invention.
Figure 2B:
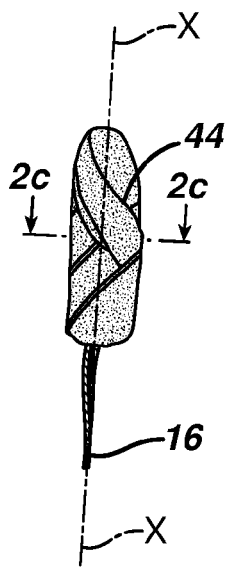
Figure 2C:
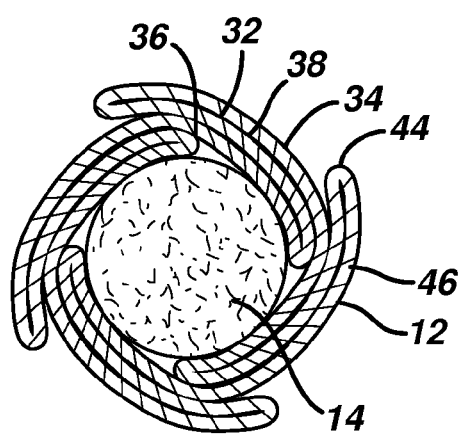
Figure 2D:
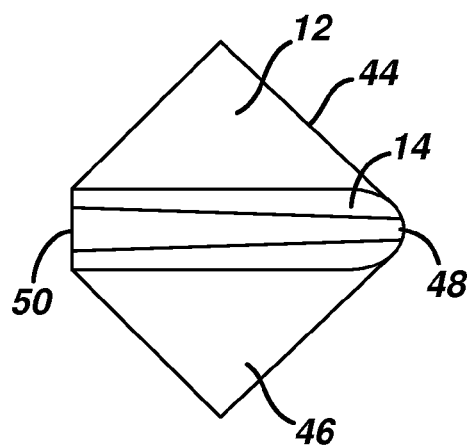
Figure 2E:
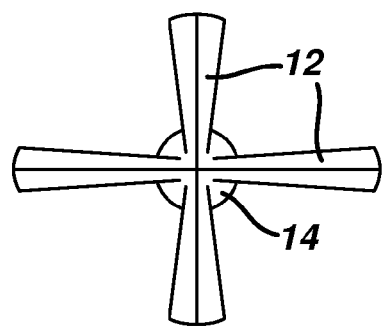
Figure 3:
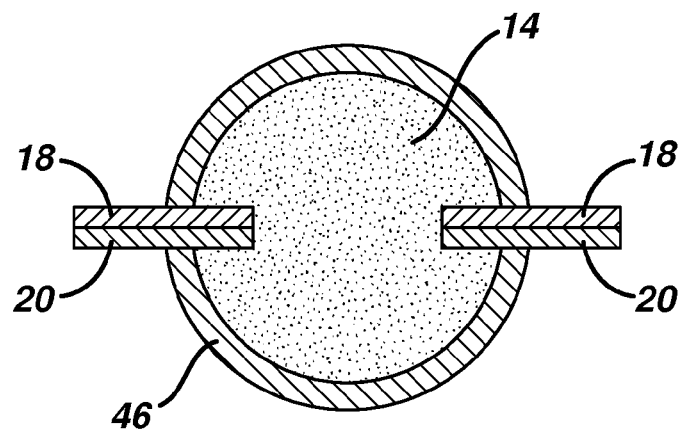
FIG. 3 shows a transverse cross-section of an alternate embodiment having a pair of fluid transport elements partially extending into the storage element.

Referring for example, to FIGS. 2 and 3, the first and second plates 18, 20 may be extensions of the same sheet-like material, e.g., formed by a fold in a sheet of material (as shown in FIGS. 2a-2c), or they may be separate elements (i.e., adjacent to each other but not necessarily joined). In a folded embodiment, the material is preferably folded to form a pleat with the first and second plates facing each other.

A preferred embodiment with pleats is shown in FIGS. 2a-2e, where the pleats 44 are folds in the cover material 46. The pleats 44 create plates that are bendable about an infinite number of bending axes ($b_{1-i}$-$b_{1-i}$) that are substantially parallel to the longitudinal axis (X-X) of the product, which longitudinal axis extends through the insertion end 48 and withdrawal end 50. These bending axes allow the plates to wrap around the product, either partially or completely. One such bending axis ($b_1$-$b_1$) is shown in FIG. 2a.

The fluid transport element 12 is in fluid communication with the fluid storage element 14 and directs fluid from the vagina to the storage element 14. Generally, fluid will be directed from each fluid transport element 12 to a particular region of the fluid storage element associated with that fluid transport element. Thus, if the device has only one fluid transport element 12, the fluid will contact the fluid storage element in one interface 52.

Therefore, additional fluid transport elements 12 directing fluid to additional locations of the fluid storage element 14 will improve the efficient usage of the fluid storage element 14. For example, two fluid transport elements 12 could be directed to opposite sides of the fluid storage element 14, as shown in FIGS. 1a-1c. Each additional fluid storage element 12 can direct fluid to additional interface locations 52 of the fluid storage element 14. For example, four evenly spaced fluid transport elements 12 allow fluid to be directed to each quarter of the fluid storage element 14 surface as shown in FIGS. 2a-e. Five or more elements would provide even more direct access. This can allow the fluid to contact the fluid storage element 14 uniformly and help to prevent or reduce local saturation of the fluid storage element 14.

While the above description provides for direct fluid communication between a fluid transport element 12 and the fluid storage element 14, direct fluid contact is not necessary. There can be fluid communication through an intermediate element, such as a porous medium (e.g., a foam or fibrous structure), a hollow tube, and the like.

Enlarging the area of the interface 52 between the fluid transport element 12 and fluid storage element 14 can also help to maximize the fluid communication. For example, elongating the interface by increasing the length of the fluid transport element 12 allows more fluid to flow into the fluid storage element 14.

The fluid transport element 12 may extend in any orientation from the surface of the fluid storage element 14. It is not necessary for the fluid transport element to be on the surface of the fluid storage element.

The inter-plate capillary gap 28 formed by first plate 18 and second plate 20 can terminate at the interface 52 or can extend into and/or through the fluid storage element 14. An example of the fluid transport element 12 extending into the fluid storage element 14 is shown in FIG. 3. The first and second plates can have additional layers on top of them as long as these additional layers allow fluid to enter the plates. The first and second plates can end at the boundary of the transport element or can extend into the fluid storage element 14.

The fluid transport element 12 may be formed to extend from the surface of the fluid storage element 14 as in FIGS. 1a-1c. It can be made in any convenient shape, including semicircular, triangular, square, hourglass etc. Additionally the two plates of the element do not have to be completely coextensive, as long as they are at least partially in a facing relationship.

Parallel plates can be held in close proximity to the storage element in a variety of ways including directly or indirectly via an additional element to the storage element. A variety of methods can be used to attach the fluid transport element 12 including but not limited to heat, adhesive, ultrasonic, sewing, and mechanically engaging the fluid storage element 14. An example of a heat-bonded attachment 54 is shown in FIG. 2a.

The fluid transport element(s) 12 can be attached at the sides, insertion end 48, and/or withdrawal end 50 of the intravaginal device. Additionally, the fluid transport element(s) 12 may be attached to themselves and not to the storage element as in a relatively loose bag covering of the storage element. The fluid transport element(s) 12 could also be attached to the withdrawal string.

The fluid transport element may be attached directly to the fluid storage element or may be attached to itself in one or more locations. Such attachment or adherence to itself or to the fluid storage element may be by any known means, including, for example, adhesive, ultrasonic, co-embossing, thermobonding, mechanical bonding (such as crimping), and the like. In one embodiment, the fluid transport element is formed of a material that is capable of being thermobonded. Alternately, the material may formed of two different materials having different melting points, at least one of which would also be capable of thermobonding.

Figure 4A:
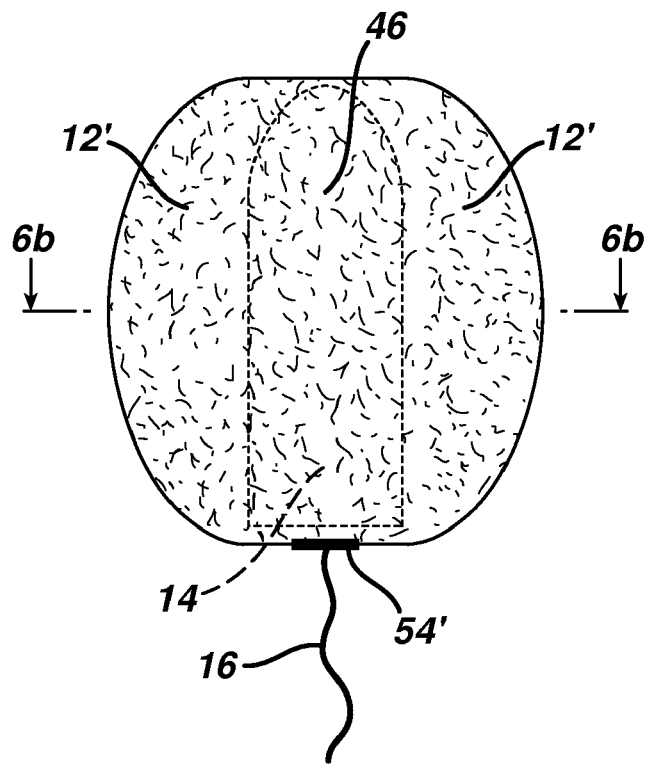
FIG. 4a shows a side elevation of an alternate embodiment of the present invention in which a cover material is bonded to itself in the form of a bag to form a fluid transport element in fluid communication with a fluid storage element.
Figure 4B:
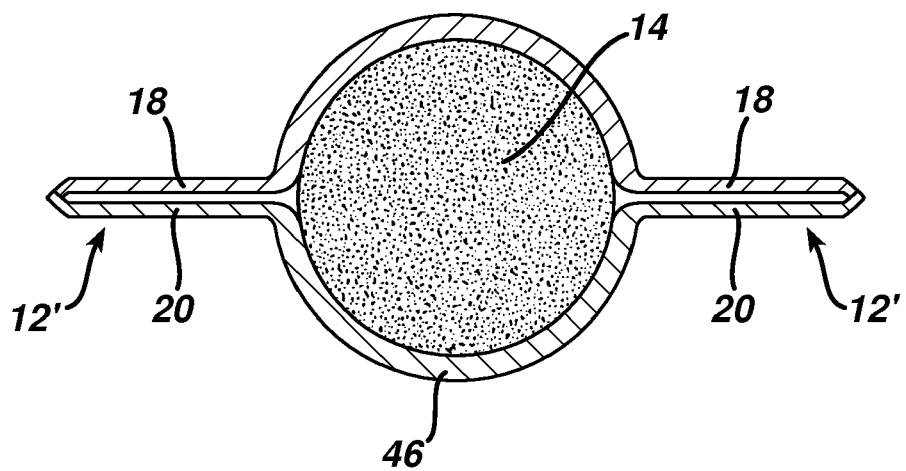
FIG. 4b shows a cross-sectional view of the device in FIG. 4a taken along line 6b-6b.

In an embodiment shown in FIGS. 4a and 4b, the cover material 46 substantially envelops the fluid storage element 14 (shown as a tampon), forming a bag or sack structure 56. This structure provides a pair of fluid transport elements 12' formed by portions of the cover material 46. In this embodiment, the cover material 46 is draped over the insertion end 48 of the tampon with the edges of the material brought together about the withdrawal end 50 and then bonded to itself 54'. The resulting fluid transport element 12' can then be folded around the tampon in the manner shown in FIG. 2b.

Figure 5:
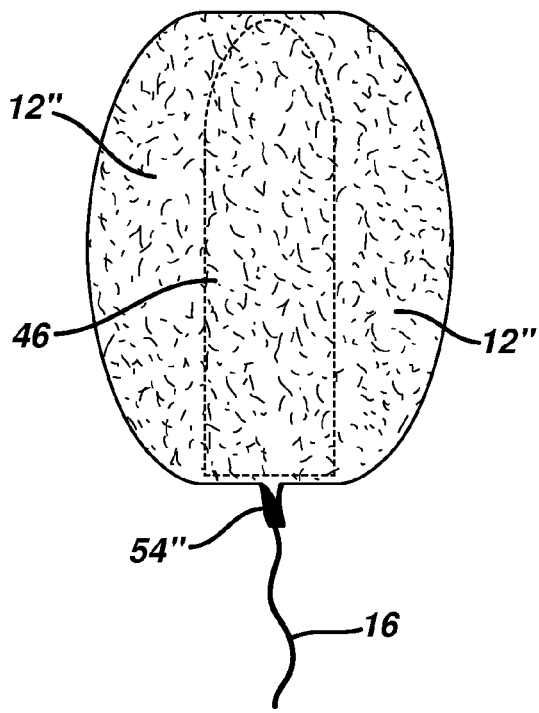
FIG. 5 shows a side elevation of an embodiment of the present invention in which the fluid transport element envelops the fluid storage element and is bonded at the withdrawal end to the withdrawal string.
Figure 6:
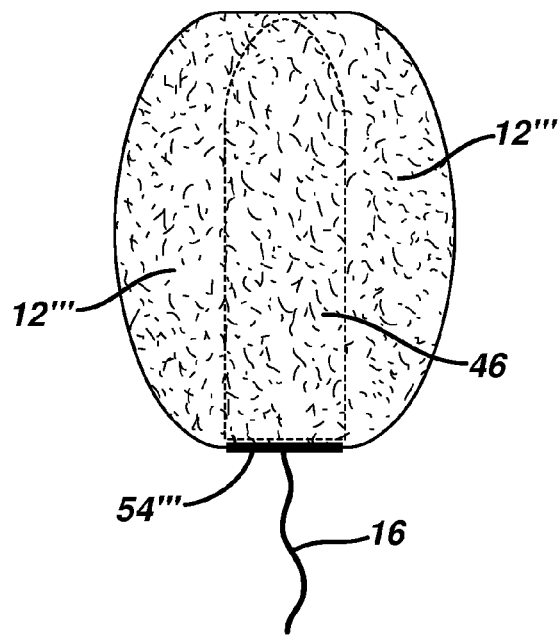
FIG. 6 shows a side elevation of an embodiment of the present invention in which the fluid transport element envelops the fluid storage element and is bonded to the base of the fluid storage element.

Other embodiments similar to that shown in FIG. 4 are possible. For example, FIG. 5 shows the attachment 54" of the fluid transport element 12 to the withdrawal string 16, and FIG. 6 shows the attachment 54''' at the withdrawal end 50, especially to the base 58 of the fluid storage element 14 (the base 58 being the generally circular surface from which the withdrawal string 16 may extend). In all of these embodiments, the cover material 46 and the associated fluid transport element 12 substantially envelop the fluid storage element 14 but do not significantly affect the performance of the fluid storage element 14. For example, if the fluid storage element 14 had been compressed and expands upon exposure to fluid, the expansion of the fluid storage element 14 would not be affected or inhibited by the attachment or bonding of the fluid transport element 12 to the fluid storage element 14.

In the embodiments described and shown in FIGS. 4-6, it is not necessary for the fluid storage element 14 to be a unitary element. For example, the fluid storage element 14 may have multiple distinct portions or segments. The segments may be attached together or may be discrete. Examples of discrete segments may be relatively loose absorbent material or compressed cellulosic tablets. However, these discrete segments could be at least partially contained to permit the fluid transport element 12 to form parallel plates, as described above.

Figure 7:
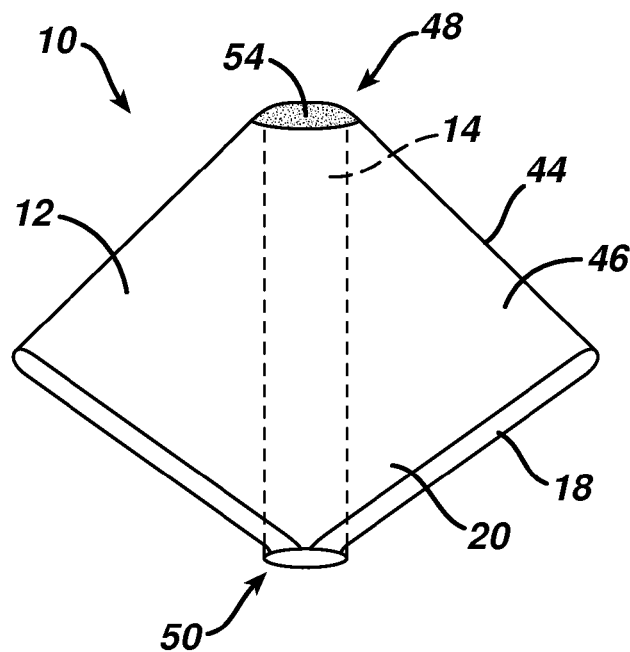
FIG. 7 shows a side elevation of an embodiment of the present invention in which the fluid transport element is attached to the insertion end of the fluid storage element.

In an alternate embodiment of the invention shown in FIG. 7, the fluid transport element 12 and the fluid storage element 14 have an attachment 54 at the insertion end 48 of fluid storage element 14. Pleats 44 formed in the fluid transport element 12 may be folded around the tampon as previously shown in FIG. 2b. Additionally, the lower portions 60 of the sheet material may also be attached to withdrawal end 50 of the fluid storage element 14, as described above and below, to prevent inversion of the fluid transport element 12 upon withdrawal.

In embodiments where the fluid transport element 12 is bonded or gathered at the withdrawal end 50 of the fluid storage element 14, it is preferable to minimize bunching of the fluid transport element 12 material to limit interference during insertion and withdrawal of the device.

Although not required, the sheet material used to form the fluid transport element 12 may initially be in a shape such that the sheet has at least one corner. The sheet material is placed over the fluid storage element 14 such that at least one portion of the sheet extends away from the fluid storage element 14. In one embodiment, the sheet has a plurality of corners, and each corner may be attached to the withdrawal end 50 of the fluid storage element 14. For example, if four sets of parallel plates are desired, the sheet material may be a square.

If the fluid storage element 14 is a compressed tampon having embossed grooves such as those disclosed in U.S. Pat. No. 5,165,152 the disclosure of which is hereby incorporated by reference, the attachment may be on the outer most surface (non-embossed) or in the grooves. Attachment may take place before, during, and/or after fluid storage element 14 compression.

Figure 8:
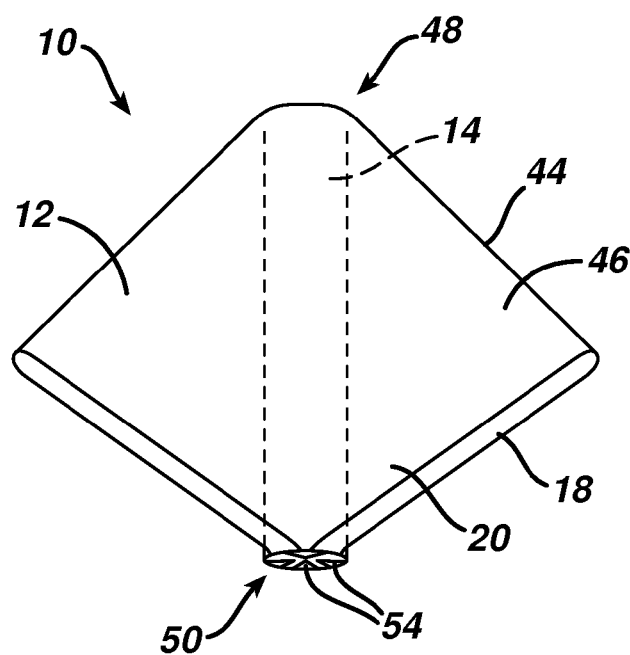
FIG. 8 shows a side elevation of an embodiment of the present invention in which the fluid transport element is bonded to the base of the fluid storage element.
Figure 9:
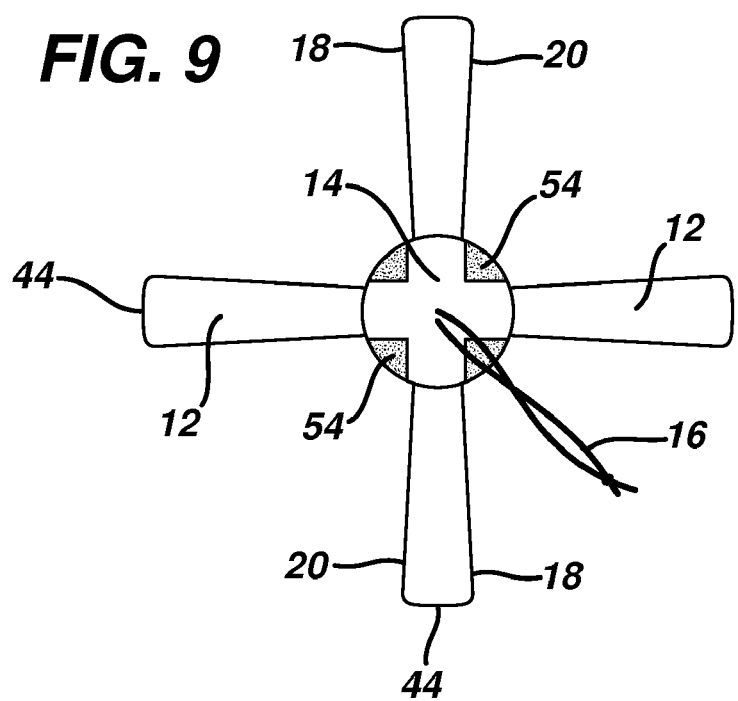
FIG. 9 shows a bottom plan view of the embodiment shown in FIG. 8.

The embodiment of FIGS. 8 and 9 is similar to that of FIG. 7. In particular, the corners of the fluid transport element 12 are attached to the base 58 of the fluid storage element 14. As seen in FIG. 9, the corners preferably do not overlap the center of the circular base 58.

When a compressed tampon having grooves 60 is used as the fluid storage element 14, it is likely that the tampon performs optimally if permitted to expand without restriction by the fluid transport element. While some compressed tampons expand due to dry expansion, others expand when exposed to fluid. One example of such a compressed tampon having grooves is the o.b.® tampon available from McNEIL-PPC, Inc., Skillman, N.J.

Figure 10:
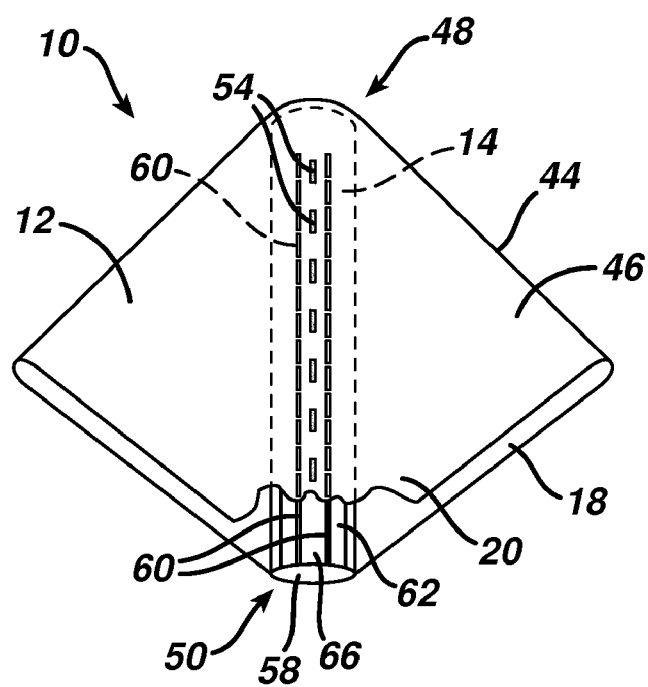
FIG. 10 shows a side elevation of an embodiment of the present invention in which the fluid transport element is bonded to the longitudinal side of the fluid storage element in a series of aligned discrete bonds.
Figure 11:
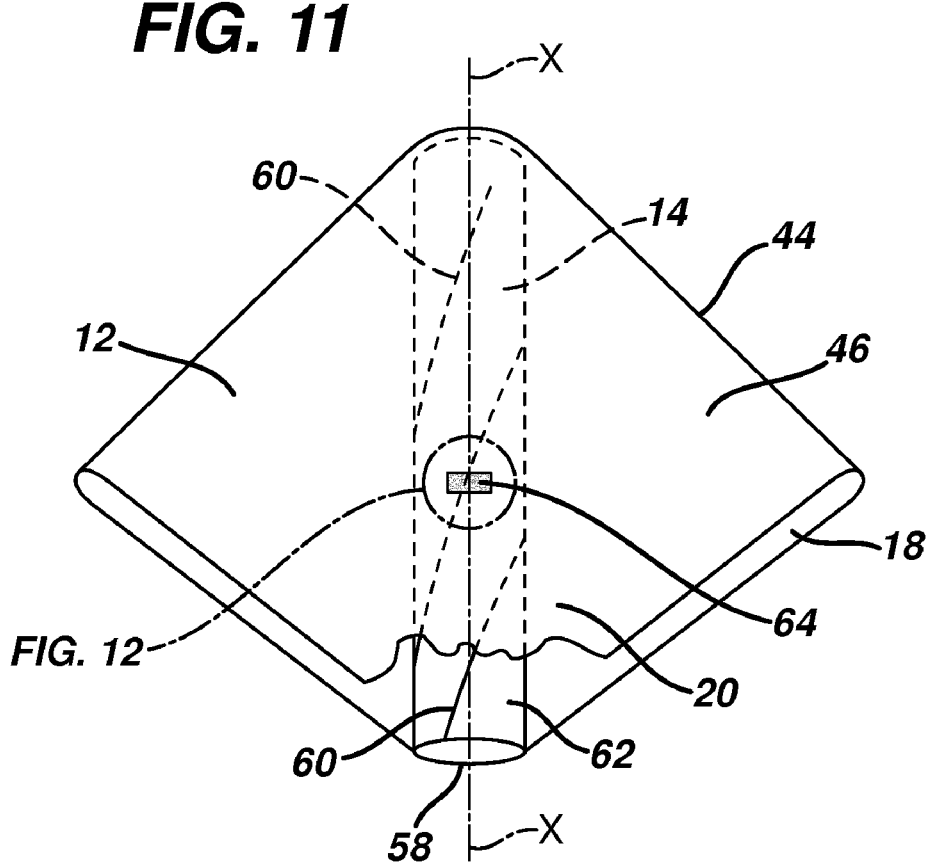
FIG. 11 shows a side elevation of an embodiment of the present invention in which the fluid transport element is bonded in at least one attachment zone having discrete spots of bonds on the longitudinal side of the fluid storage element.
Figure 12:
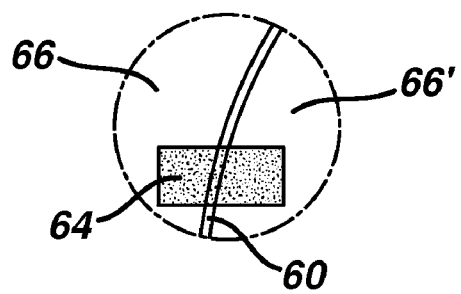
FIG. 12 shows an enlarged view of a section of the embodiment shown in FIG. 11.

In the embodiments shown in FIGS. 10-12, the fluid storage element 14 is a compressed tampon having an exterior surface 62 and grooves 60. Grooves 60 have an interior portion, which becomes part of the exterior surface 62 of the tampon upon absorption of fluids and the resultant tampon expansion. Because the fluid transport element 12 is attached to the exterior surface 62 of the tampon at its withdrawal end 50, it does not extend into the tampon grooves 60. Thus, the fluid storage element 14 may expand without any interference from the fluid transport element 12. In other words, the fluid transport element 12 does not significantly limit the functionality of the fluid storage element 14. Pleats 44' form in the fluid transport element 12 and may be similarly folded around the tampon as previously shown in FIG. 2b.

As shown in FIG. 10, a tampon having straight grooves is attached to the fluid transport element 12 using a series of heat bonds 54 along one or more single line(s) along the tampon. This provides easier alignment of the attachment 54 and the exterior surface 62 of the tampon as the bond line may be registered accurately to avoid coinciding with the grooves 60. Thus, the fluid transport element 12 may be readily attached along the longitudinal side without interfering with the expansion of the tampon.

In a similar embodiment shown in FIGS. 11 and 12, the fluid transport element 12 may be attached along the longitudinal side of a tampon having spirally oriented grooves. In this embodiment an attachment zone 64 of fluid transport element 12 extends from one lobe 66 and across groove 60 to adjacent lobe 66'. Materials such as nonwoven webs have a certain amount of elasticity and may be designed to permit the tampon expansion, especially the material located within the interior portion of the grooves 60.

If desired, the attachment zone 64 may be oriented in any direction relative to the longitudinal axis X-X of the fluid storage element 14. As shown in FIGS. 11 and 12, the attachment zone 64 comprises a matrix or other grouping of discrete bonds, such as dots or spots. This allows the interface between the fluid transport element 12 and the fluid storage element 14 to remain as open to fluid flow as possible.

Figure 13:
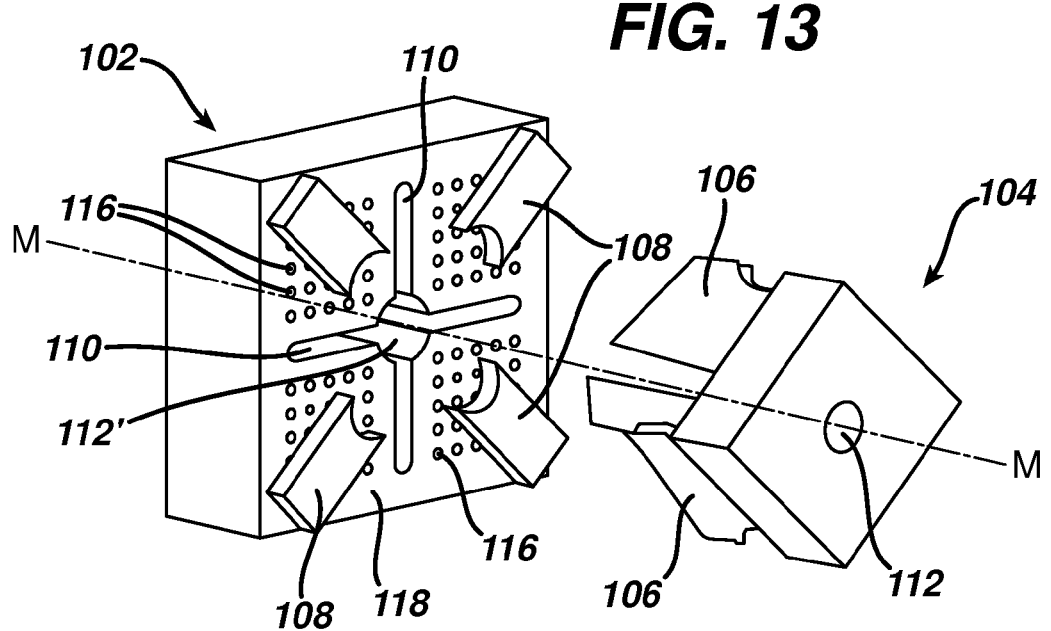
FIG. 13 shows a schematic perspective view of apparatus according to the present invention useful to manufacture an intravaginal device.
Figure 14:
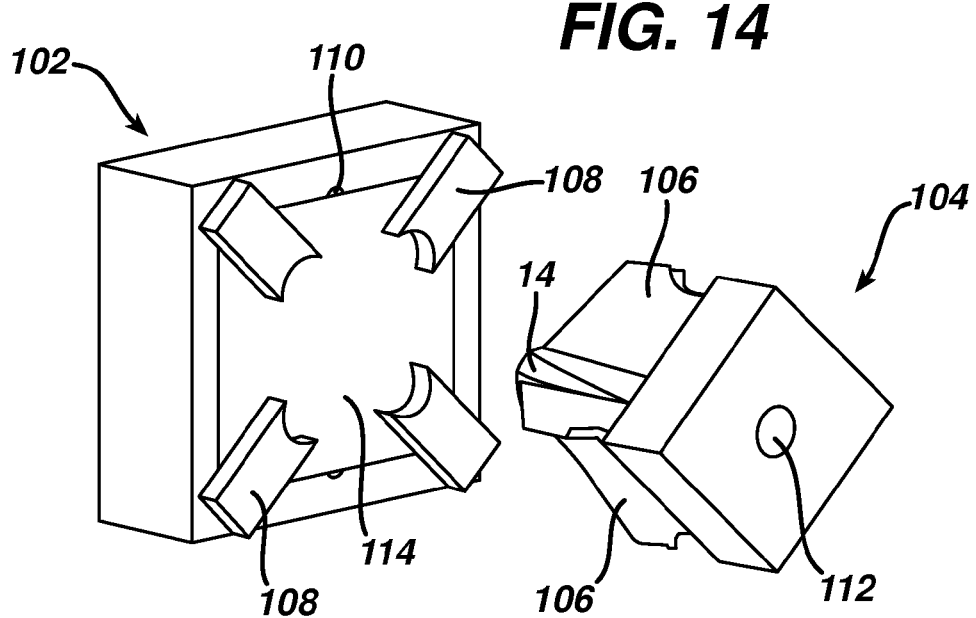
FIG. 14 shows the schematic perspective view of apparatus of FIG. 13 including a fluid storage element and a sheet of material prior to formation of the fluid transport element.

As previously mentioned and shown, the fluid transport element 12 may be attached to the fluid storage element 14 be any number of methods and embodiments. For example and with reference to FIGS. 13-15, a tampon may be manufactured as shown in Friese, U.S. Pat. No. 4,816,100, and either Friese et al., U.S. Pat. No. 6,310,269, or Leutwyler et al., U.S. Pat. No. 5,911,712. However, after the tampon is formed and prior to packaging, an additional process employing a forming tool 102, a male tool 104 having a plurality of blades 106, and thermobonding elements 108 applies a fluid transport element 12 to the fluid storage element 14. The tools are aligned in a manner that the blades 106 of the male tool 104 cooperate with corresponding slots 110 in the forming tool 102. In addition, each of the tools has a central aperture 112, 112' through which a fluid storage element 14 may pass during processing.

In somewhat more detail, an individual sheet 114 of material is separated from a supply (not shown) and placed on the forming tool 102. A vacuum is drawn across the forming tool 102 via a plurality of vacuum ports 116 on the face 118 of the forming tool 102 to hold the individual flexible sheet 114 in place.

Figure 15:
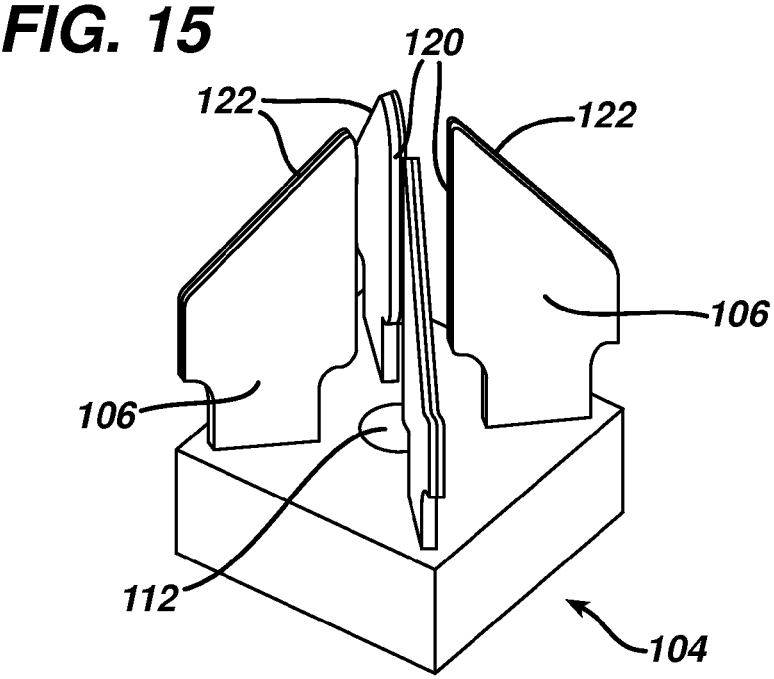
FIG. 15 shows a schematic perspective view of a male tool useful in the apparatus of FIG. 13.

The blades 106 of the male tool 104 are shown arranged radially about the central aperture 112 in the male tool 104 (as shown in FIG. 15). The blades 106 cooperate to hold the fluid storage element 14 in line with the central aperture 112. A pushrod (not shown) is arranged to penetrate the central aperture 112 of the male tool 104 and to bear on the base of the fluid storage element 14. In the preferred embodiment shown in FIGS. 13-15, four blades 106 are arranged at equal angles about the central aperture 112. Each blade 106 provides a guide edge 120 facing the fluid storage element 14 (when present) and a pleating edge 122 disposed radially outwards from the guide edge 120. The pleating edge 122 may be an edge that is adjacent the guide edge 120, or it may be separated by one or ore intermediate portions of the blade 106.

In operation, the male tool 104 holding a fluid storage element 14 is moved along the machine axis (M-M) aligned with the central apertures 112, 112' toward the forming tool 102 carrying the individual flexible sheet 114. The insertion end 48 of the fluid storage element 14 contacts the individual flexible sheet 114 and urges it through the central aperture 112' of the forming tool 102. The pleating edges 112 of the blades 106 urge corresponding portions of the individual sheet 114 through the slots 110 of the forming tool 102 creating four sets of parallel plates 18, 20.

Once the fluid storage element 14 is inserted into the central aperture 112' of the forming tool 102 with only a portion of the withdrawal end 50 remaining exposed, thermobonding elements 108 extend into the space between the blades 106 to bond the four corners of the individual sheet 110 to the exterior surface 62 of the fluid storage element 14, forming the fluid transport element 12. The pushrod may then continue to move the insertable device 10 into and through the central aperture 112' of the forming tool 102. The fluid transport element 12 may then be folded about the fluid storage element 14. The resulting insertable device may then be packaged in a hygienic overwrap as is well known in the art.

In another embodiment shown FIGS. 19-25, the fluid transport element may be attached to the fluid storage element by alternate methods.

Figure 19:
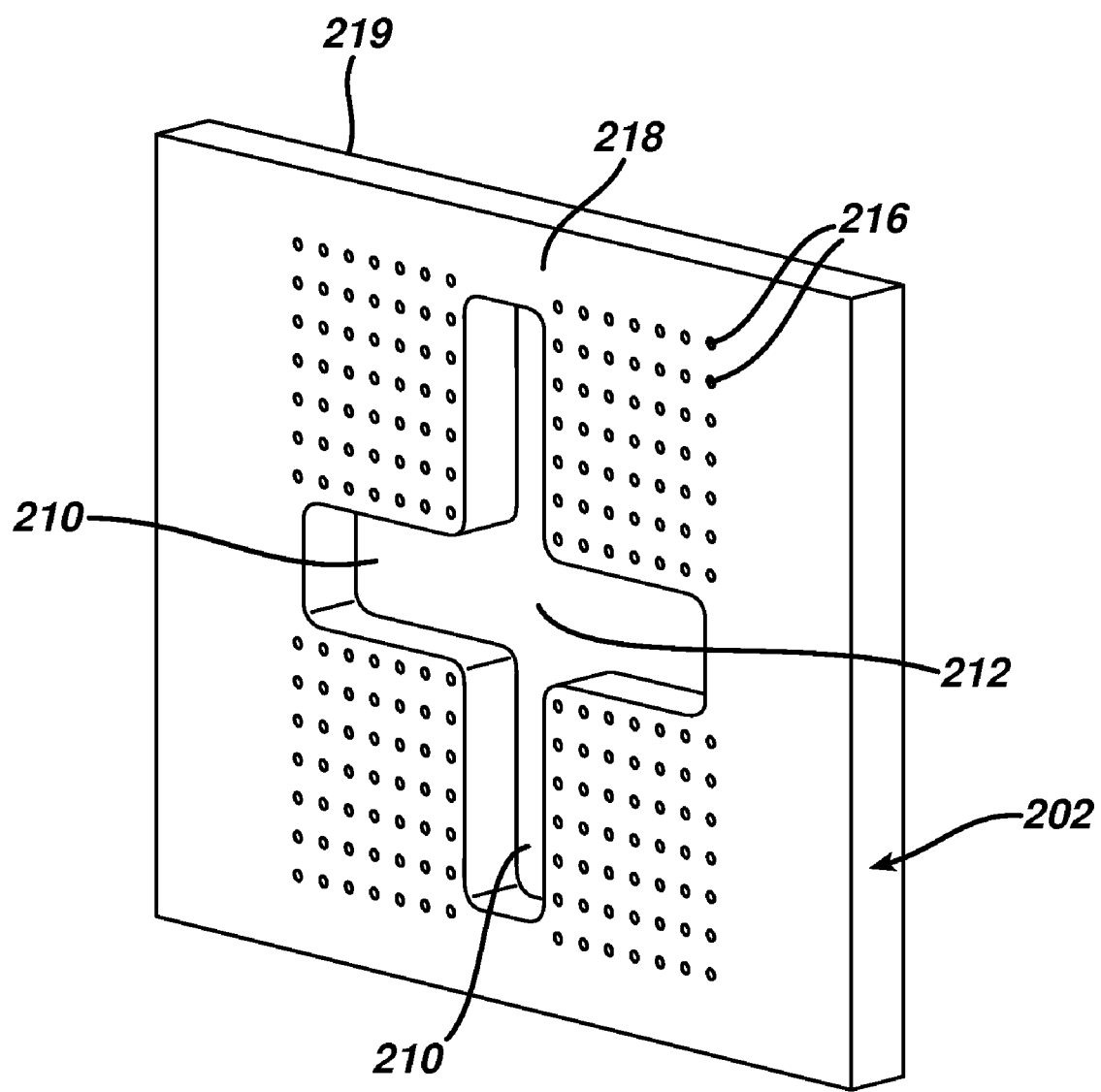
FIG. 19 shows a schematic perspective view of an alternate embodiment of a male tool useful in the apparatus of FIGS. 22-24.
Figure 20:
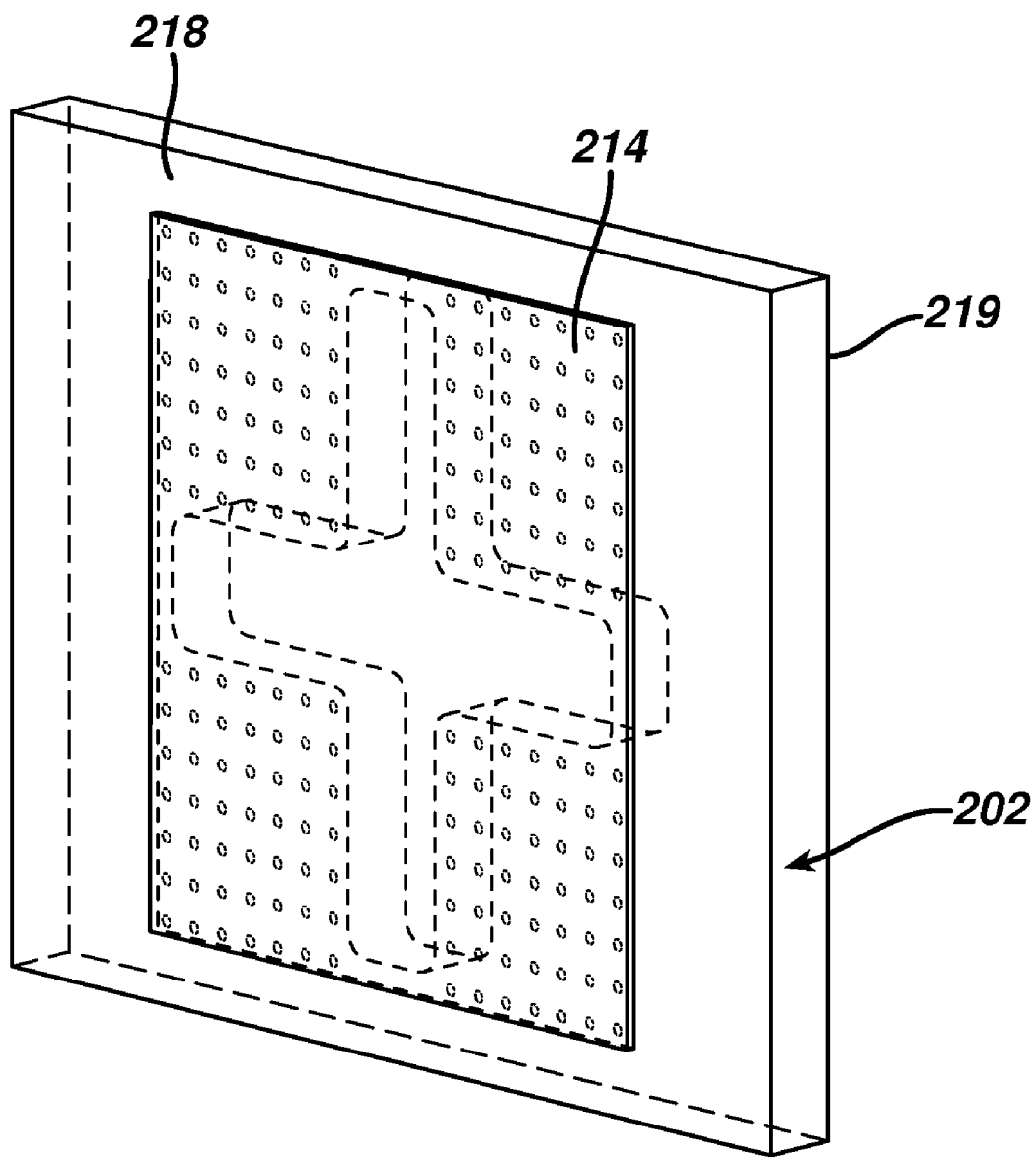
FIG. 20 shows a schematic perspective view of the male tool of FIG. 19 with sheet 114 in place.

In somewhat more detail as shown in FIGS. 19 and 20, an individual sheet 114 of material is separated from a supply (not shown) and placed on the holding plate 202. Holding plate 202 has a first side 218 and a second side 219. A vacuum is drawn across the holding plate 202 via a plurality of vacuum ports 216 on the first side 218 of the holding plate 202 to hold the individual sheet 114 in place (shown FIG. 20). Holding plate passageway 212 provides an opening from the first side 218 through the holding plate to the second side 219. Holding plate passageway may include at least one slot 210 or any number of slots, which corresponds to the number of forming blades of the male and female forming tools. The central portion of the passageway 212 of the holding plate may also include a central clamp (not shown) or other means to secure the sheet 114 against leading portion 324 of the male forming tool 304 once the leading edge of fluid storage element 14 has contacted sheet 114.

Figure 21:
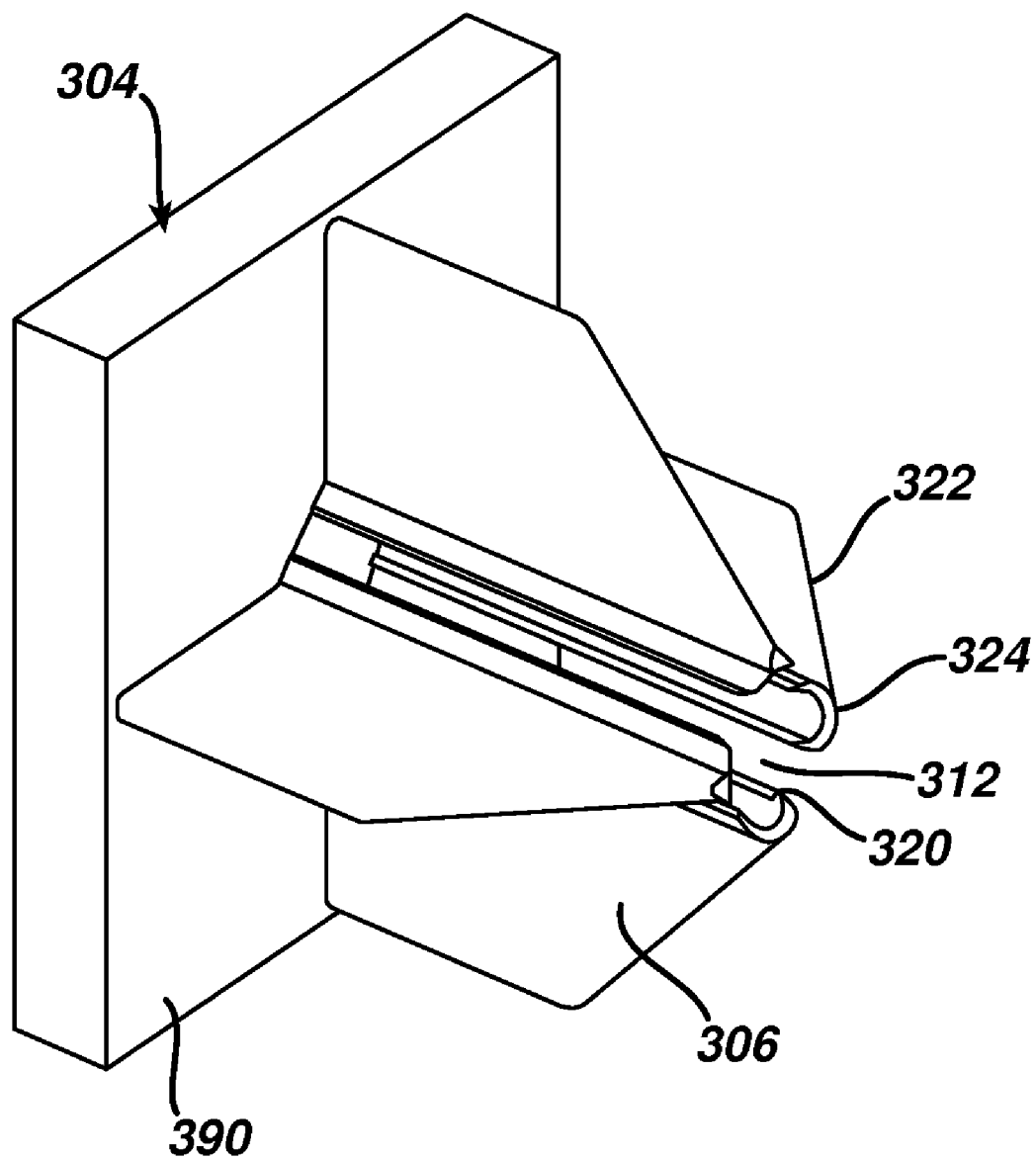
FIG. 21 shows another perspective view of the male tool of FIG. 19 attached to a holding block.

Turning to FIG. 21, pleating blades 306 are shown arranged radially about central aperture 312 and secured to holding block 390 in male tool 304. For clarity, holding block 390 is shown only in FIG. 21. The end of the blade that is opposite the holding block 390 is leading portion 324. Pleating blades 306 cooperate to hold the fluid storage element 14 in line with the central aperture 312 (shown FIG. 22-23). In a preferred embodiment shown in FIGS. 21-23, four pleating blades 306 are arranged at equal angles about the central aperture 312. Each pleating blade 306 provides a guide edge 320 facing the fluid storage element 14 (when present) and a pleating edge 322 disposed radially outwards from the guide edge 320. The pleating edge 322 may be an edge that is adjacent to the guide edge 320, or it may be separated by one or more intermediate portions of the blade 306. While the preferred embodiment shown in the figures employs four pleating blades, the male tool may have any number of pleating blades including one. The thickness of the blade 306 may range from about 0.5 mm to about 10 mm and may have any shape. In one embodiment, the thickness of each pleating blade is uniform. In another embodiment, the pleating blade increases in thickness from the guide edge 320 toward the outer edges. In another embodiment, the pleating blade thickness decreases from the guide edge 320 to the outer edges. In still another embodiment, the thickness of the pleating blade increases from the leading edge to the end. In yet another embodiment, the thickness decreases from the leading edge to the end.

The guide edge 320 helps to align the fluid storage element 14. In one embodiment, the surface of the fluid storage element 14 has lobes and grooves (not shown). In this application, the guide edge may be designed such that the guide edge actually engages at least one groove. For example, the guide edge may have two portions that span the lobe and fit into the upper portion of the groove. This arrangement would secure the fluid storage element within the central aperture 312 allowing for the fluid storage element to be positively oriented along the M-M axis and ensure that the sealing area is confined to a specific predetermined area of the tampon. In another embodiment, the guide edges may orient the fluid storage element such that the groove(s) may be aligned with the sealing element(s). If the fluid storage element has another configuration, for example, is a tampon with spiral grooves, the guide edge may be a flat surface.

Female tool 402 (shown in detail in FIG. 25) has at least one pair of folding blades 408. In a preferred embodiment, there are four pairs of folding blades, 408. The folding blades 408 may be arranged about the central aperture 414. Each folding blade 408 has a pair of members 412. The folding blades have a first end 428 and back end 438. The first end 428 of folding blade 408 moves through passageway 212 of holding plate 202 (shown FIG. 22). The back end 438 of each blade 408 is joined to female base 430. In the embodiment shown, the leading edge of first end 428 is angled. Although an angled edge is preferred, other configurations are possible.

Each pair blade pair 408 are aligned to the male forming blades such that in use, blade 306, along with sheet 114, fits within the gap 410 between folding blade pair 408. The distance between folding blade pair 408 (gap 410) can range from about 0.7 mm to about 12 mm.

Figure 22:
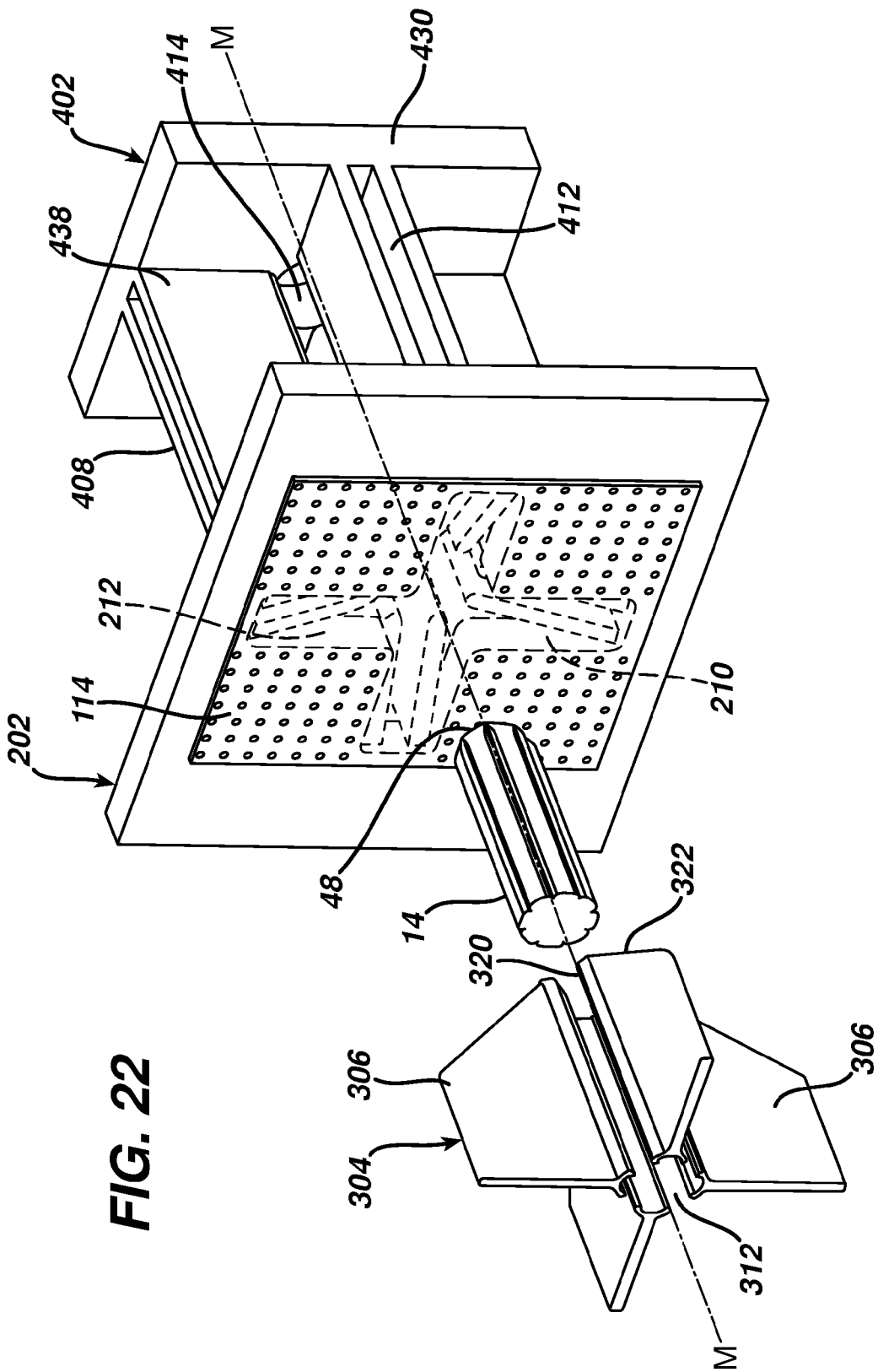
FIGS. 22-24 show schematic views of an apparatus according to the present invention useful to manufacture an intravaginal device.
Figure 23:
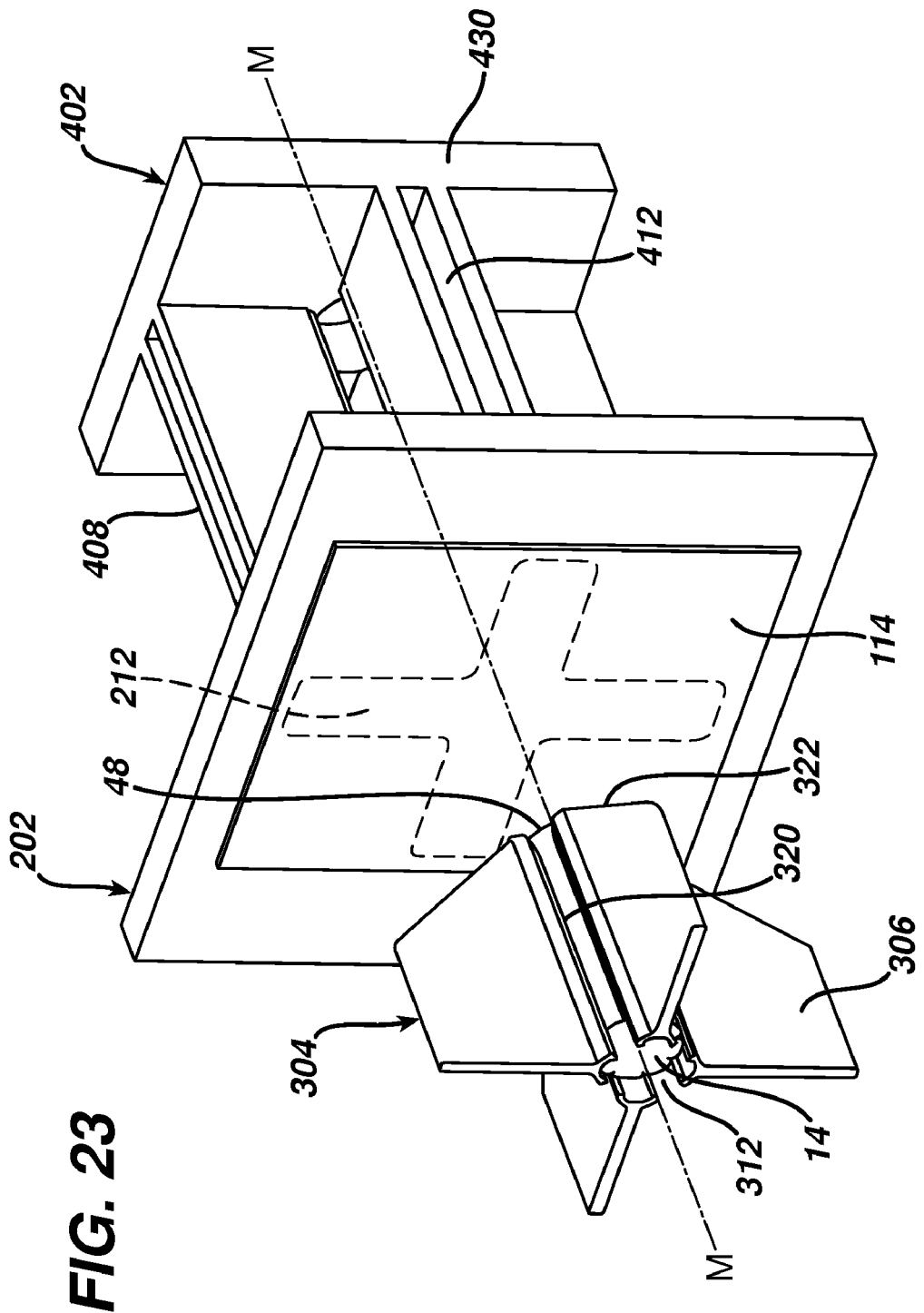
Figure 24:
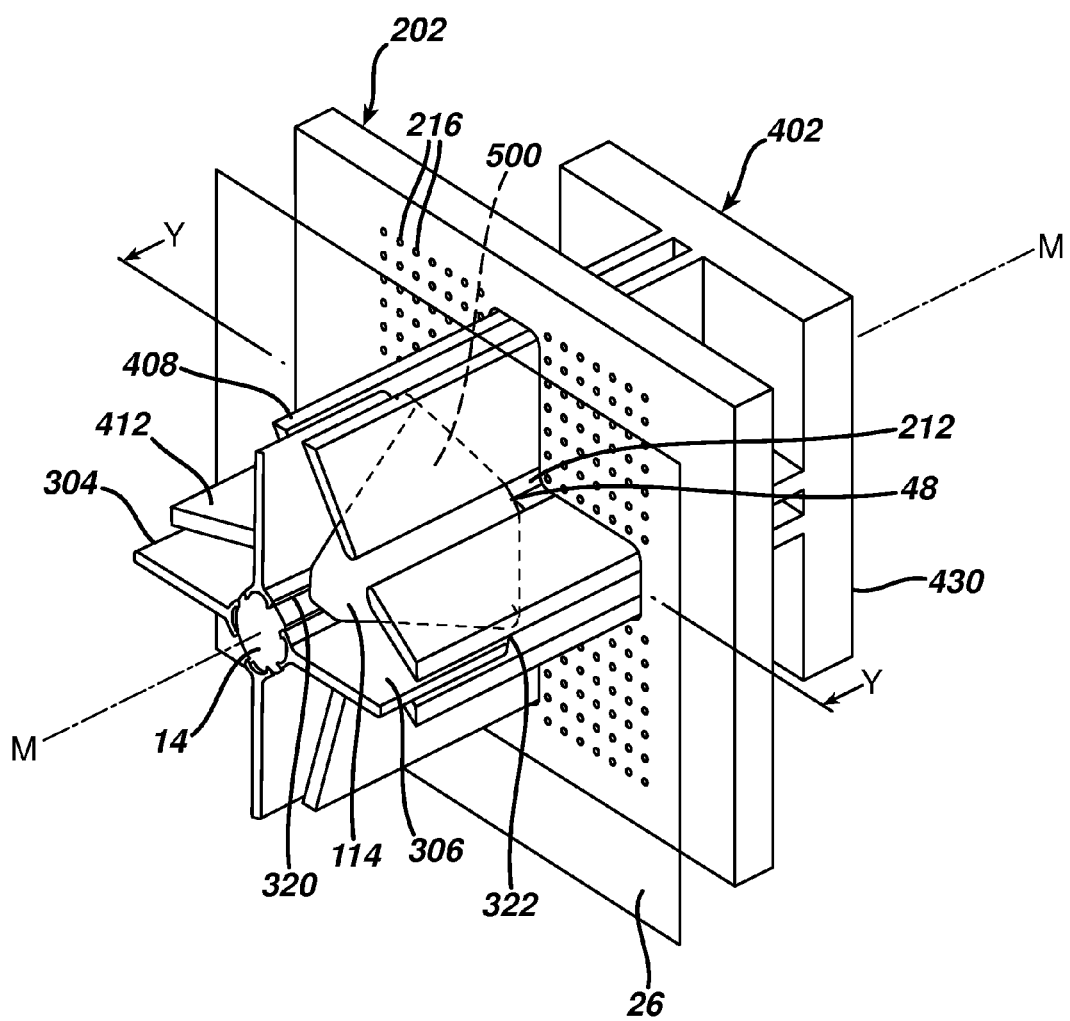
Figure 25:
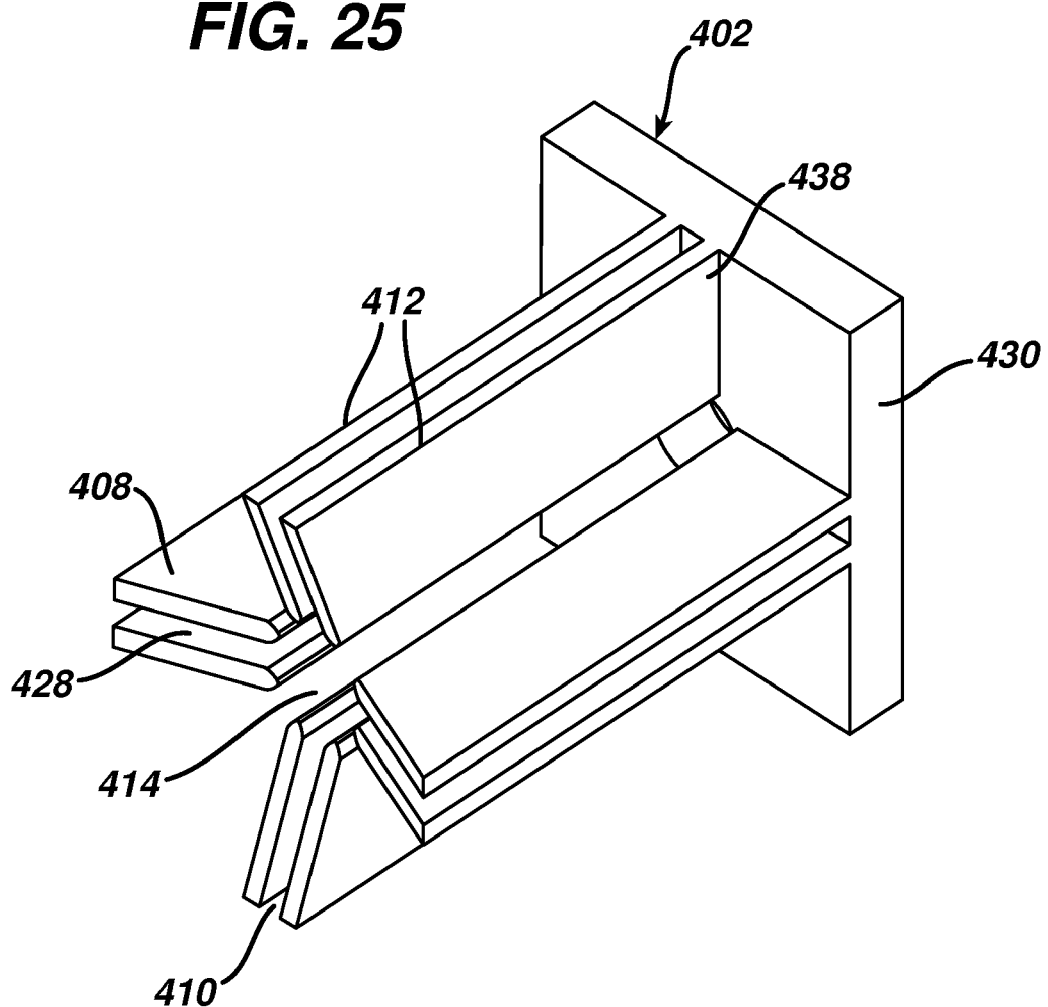
FIG. 25 shows a schematic perspective view of a female tool useful in an alternate embodiment of the invention.

In a preferred embodiment shown in FIGS. 22-24, female tool 402 and male tool 304 are located on the opposite sides of holding plate 202 and aligned with passageway 212. In an alternative embodiment, female tool 402 and holding plate 202 form a single structure (not shown) such that female tool 402 is moveably attached to holding plate 402 at passageway 212, thereby capable of moving to a withdrawn position where the first end 438 of folding blade 408 does not distort the individual sheet 114 as it is held on holding plate 202.

In operation, an individual sheet 114 of material is placed on the holding plate 202. The male tool 304 holding a fluid storage element 14 is moved along the machine axis (M-M) aligned with passageway 212 of holding plate 202. In one embodiment, the insertion end 48 of the fluid storage element 14 contacts the individual sheet 114 and stops.

The folding blades 408 of female tool 402, also aligned with machine axis (M-M) and passageway 212 of holding plate 202, extend through passageway 212 while the holding plate 202 remains stationary. The individual sheet 114 will begin to buckle as the sheet is pushed over the pleating edges 322 of pleating blades 306. As the folding blades 408 move further through the passageway 212 of the holding plate 202, sheet 114 is urged over the pleating edges 322 of the pleating blades 306 creating a pleat 500.

Figure 26:
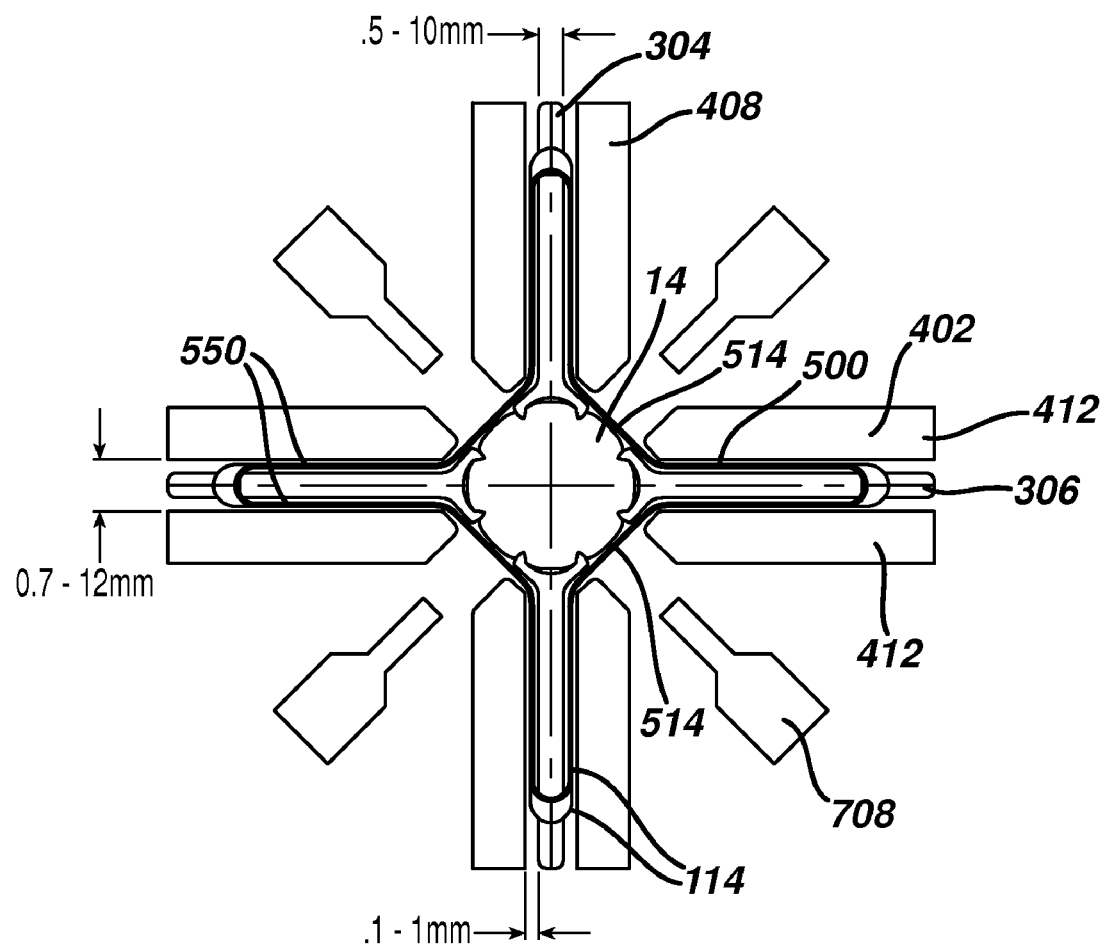
FIG. 26 shows a cross-sectional view taken along lines Y-Y of FIG. 24.

As shown in FIG. 26, a portion 514 of sheet 114 is juxtaposed next to fluid storage element 14. This portion is adjacent to pleat 500 and lies along a longitudinal side of fluid storage element 14. Portion 514 is not covered by female tool 402 or male tool 304 but rather left exposed for further processing. A portion of sheet 114 that contacts the insertion end and withdrawal end of fluid storage element is included in portion 514.

Once the female tool 402 has completed moving and formed pleat 500, thermobonding elements 708 extend into the space between the pleating blades 306 to bond within the exposed portion 514. The thermobonding may take any design such as a continuous seal line, straight, curved, sigmoidal, etc. or the thermobonding may be a series of non-continuous bonds. When the thermobonding occurs, pleat 500 forms fluid transport element 12 having parallel plates 550. In one embodiment, sheet 114 is thermobonded to the external surface of fluid storage element 14. Bonding of the fluid transport element to the fluid storage element may determine how the fluid storage element expands once exposed to fluid. For example, if the fluid transport element is bonded to a lobe, the fluid storage element may expand uninhibited. If, however, the bonding goes across a groove, then the expansion may be limited. While thermobonding is a preferred way to bond the fluid transport element to the fluid storage element, other ways are possible and will be apparent to those skilled in the art. For example, the fluid transport element may be joined to the fluid storage element by ultrasonic means, hot air, adhesive, and the like.

FIG. 26 shows a cross-sectional view of FIG. 24 taken along plane 26 with thermobonding units 708 in position to contact sheet 114. In this view, one can see the relationship of the folding blades 408 to the pleating blades 306. Sheet 114 is positioned within the space between the blades with members 412 on either side of pleating blade 306. In an embodiment previously discussed, this figure also shows the guide edge 320 of pleating blade 306 engage in a groove and thereby securing the fluid storage element 14.

In another embodiment (not shown) for making a fluid management device, the passageway of the holding plate has an opening with two opposed slots (or one continuous slot extending the length of two opposed slots) as shown in FIGS. 19 and 20. In this process, two pleats are initially formed in the sheet and attached to the fluid storage element in a single step via seals on opposite side surfaces of the fluid storage element. The resulting product continues to a second pleating station in which the remaining pleats are formed and attached to the side surface of the fluid storage element. One of ordinary skill in the art will recognize that this process can be repeated to create additional pleats. In one preferred embodiment of this method, the resultant absorbent device then has four formed pleats.

While the process described above in reference to FIGS. 13-15 and 22-26 employs pleating blades 306 that have a guide edge 320 that is shorter than the fluid storage element 14, this relationship may be altered. For example, the pleating blades 306 could be modified to have a guide edge 320 that is longer than the fluid storage element 14 or the system could otherwise be modified to allow the leading portions 324 to contact the individual sheet 114, first. This permits the formation of a small gap between the insertion end 48 of the fluid storage element 14 and the individual sheet 114 that may allow more free expansion of the fluid storage element without restriction by the fluid transport element 12 during use.

Figure 16:
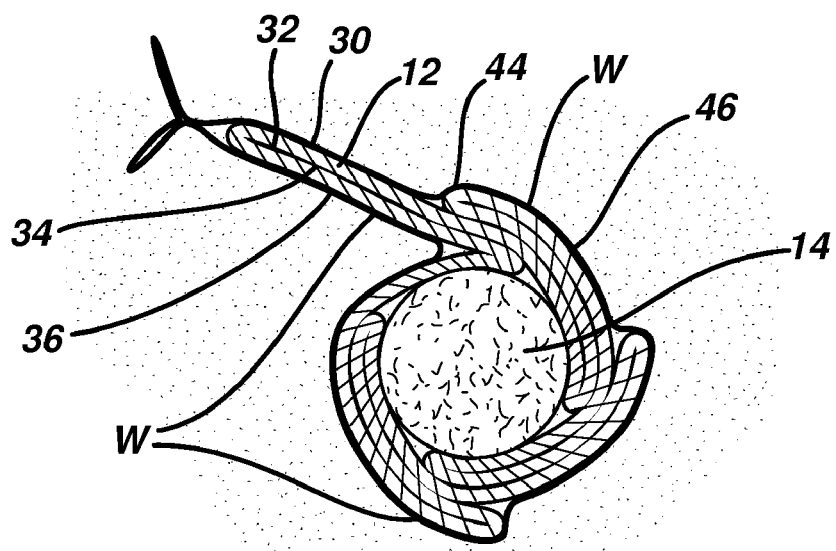
FIG. 16 shows a transverse cross-section of a human vagina with an intravaginal device according to FIG. 2b disposed therein with one fluid transport element extending away from the fluid storage element.
Figure 17:
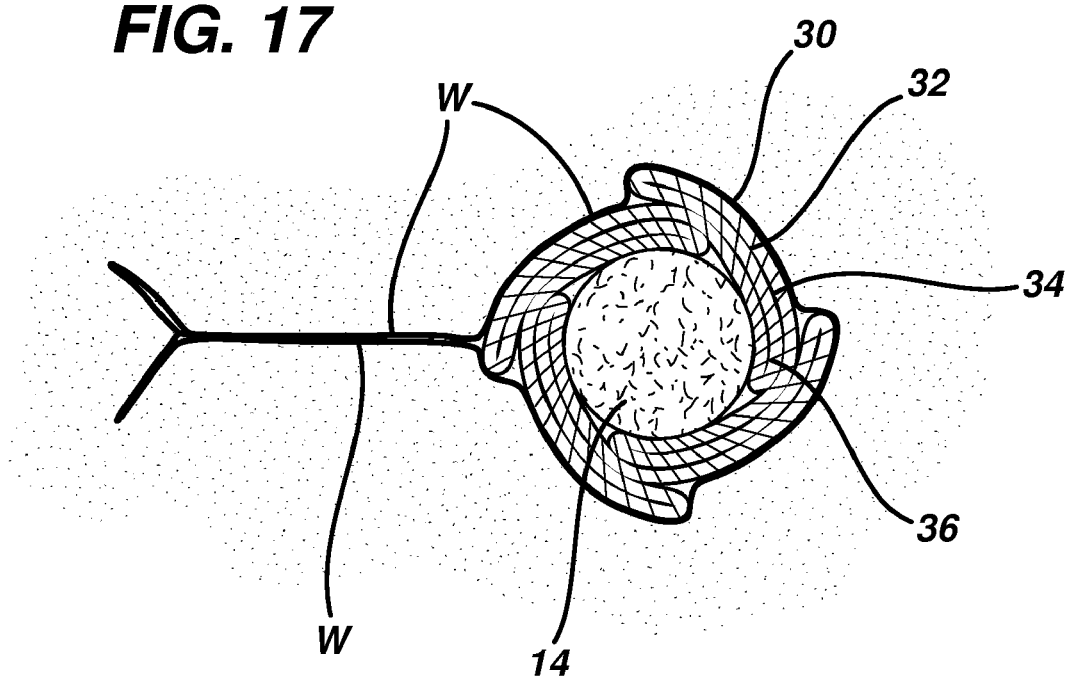
FIG. 17 shows a transverse cross-section of a human vagina with an intravaginal device according to FIG. 2b disposed therein with the fluid transport elements remaining wrapped around the fluid storage element.

During use, fluid transport element(s) 12 can take on many configurations within the vagina. For example, a fluid transport element 12 may extend into the vagina away from the fluid storage element 14, as shown in FIG. 16. Alternatively, and the fluid transport element(s) 12 may remain wound about the fluid storage element 14, contacting the vaginal wall "W" only through the first surface 30 (FIG. 17).

A withdrawal mechanism, such as withdrawal string 16, is preferably joined to the intravaginal device 10 for removal after use. The withdrawal mechanism is preferably joined to at least the fluid storage element 14 and extends beyond at least its withdrawal end 50. Any of the withdrawal strings currently known in the art may be used as a suitable withdrawal mechanism, including without limitation, braided (or twisted) cord, yarn, etc. In addition, the withdrawal mechanism can take on other forms such as a ribbon, loop, tab, or the like (including combinations of currently used mechanisms and these other forms). For example, several ribbons may be twisted or braided to provide parallel plates structures.

Tampons are generally categorized in two classes: applicator tampons and digital tampons, and a certain amount of dimensional stability is useful for each type of tampon. Applicator tampons use a relatively rigid device to contain and protect the tampon prior to use. To insert the tampon into a body cavity, the applicator containing the tampon is partially inserted into the body cavity, and the tampon can be expelled from the applicator into the body cavity. In contrast, digital tampons do not have an applicator to help guide them into the body cavity and require sufficient column strength to allow insertion without using an applicator.

While the applicator tampon is protected by the rigid applicator device and the applicator tampon need not as have as high a degree of column strength as a digital tampon, applicator tampons do require dimensional stability (especially radial) to be acceptable for use. This dimensional stability provides assurance, for example, that the tampon will not prematurely grow and split its packaging material or become wedged in a tampon applicator.

Figure 18:
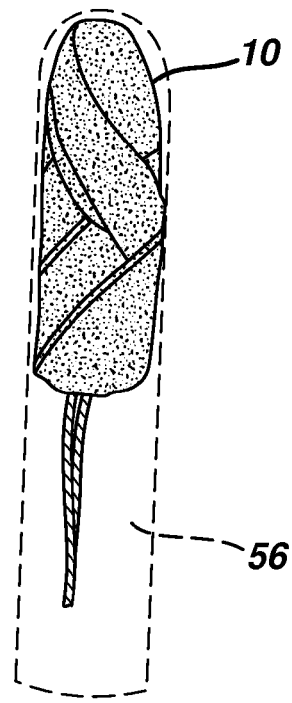
FIG. 18 shows the device of FIG. 2 contained in an applicator device packaging element.

Further, the intravaginal device can be collapsed for packaging and insertion. For example, at least a portion of a major surface of the fluid transport element 12, such as the first surface 30, may be in contact with at least a portion of an outer surface of the fluid storage element 14. This can be achieved by wrapping the fluid transport element(s) around the fluid storage element 14 (as shown in FIG. 2c). Alternatively, the fluid transport element(s) 12 may be folded or pleated (e.g., in an accordion-like manner) against the fluid storage element 14. The thus-compacted device can then be packaged, (e.g., within an applicator or alone in a wrapper). FIG. 18 shows a wrapped tampon within an applicator 68 (in phantom).

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of producing an intravaginal device comprising the steps of:

a) placing a substantially cylindrical fluid storage element in a central cavity of a male tool disposed along a machine axis, the male tool comprising a plurality of pleating blades extending in a direction radially away from the machine axis, each of the plurality of pleating blades is spaced at a uniform radial distance from the machine axis to define the central cavity;

b) folding a flexible sheet about the male tool and the fluid storage element by means of relative motion of a female tool disposed along the machine axis, the female tool comprising a plurality of folding elements extending from a base portion proximate the machine axis in a direction radially away from the machine axis, each folding element comprising a pair of folding blades separated by a folding element gap sufficient to accept a corresponding pleating blade of the male tool, and each folding element is spaced at a uniform radial distance from the machine axis to define a central cavity of the female tool; and c) moving an attachment tool into a gap defined by spaced apart bases of adjacent folding elements to attach at least a portion of the flexible sheet to at least a portion of a side of the fluid storage element such that portions of the flexible sheet that are folded about the pleating blades of the male tool extend away from the fluid storage element.

2. The method of claim 1, wherein the step of moving the attachment tool to attach the flexible sheet to the fluid storage element comprises applying heat and pressure to the flexible sheet and fluid storage element.

3. The method of claim 1, further comprising the step of folding the portions of the flexible sheet that extend away from the fluid storage element about an axis parallel to the machine axis.

4. The method of claim 3, wherein the step of folding the flexible sheet comprises convolutedly winding the flexible sheet portions about side surface of the fluid storage element.

5. The method of claim 1, further comprising the step of separating a flexible sheet from a supply of nonwoven material having properties useful to move bodily fluids.

6. The method of claim 1, further comprising the step of holding a flexible sheet on a holding tool disposed between the male tool and female tool comprising:

a) a generally planar holding face disposed toward the male tool and oriented substantially perpendicular to the machine axis;

b) an aperture aligned along the machine axis and extending from the holding face, the aperture comprising a central portion of substantially circular cross section disposed uniformly about the machine axis and a plurality of slots having a generally rectangular cross section extending radially outwards from the central portion; and c) means for holding a flexible sheet across the aperture.

7. The method of claim 6, further comprising the step of providing a pressure differential at the holding face to hold the flexible sheet across the aperture.

* * * * *

UNITED STATES PATENT AND TRADEMARK OFFICE
CERTIFICATE OF CORRECTION

PATENT NO. : 8,028,500 B2  
APPLICATION NO. : 12/724739  
DATED : October 4, 2011  
INVENTOR(S) : Curt Binner Page 1 of 1

It is certified that error appears in the above-identified patent and that said Letters Patent is hereby corrected as shown below:

Title page, (63) Related U.S. Application Data should read:

Divisional of application No. 11/478,944, filed on Jun. 30, 2006, now Pat. No. 7,861,494, which is a continuation-in-part of application No. 11/444,792, filed on Jun. 1, 2006, now Pat. No. 7,845,380, ~~which~~ and is a continuation-in-part of application No. PCT/US2005/017107, filed May 13, 2005, ~~which~~ and is a continuation-in-part of application No. 10/848,257, filed on May 14, 2004, now abandoned, ~~which~~ and is a continuation-in-part of application No. 10/847,951, filed on May 14, 2004.

Signed and Sealed this
Twenty-ninth Day of November, 2011

David J. Kappos
*Director of the United States Patent and Trademark Office*